(12) United States Patent
Diperna et al.

(10) Patent No.: US 12,178,998 B2
(45) Date of Patent: Dec. 31, 2024

(54) MEDICAL PUMP WITH FLOW CONTROL

(71) Applicant: QUASURAS, INC., Escondido, CA (US)

(72) Inventors: Paul M. Diperna, Escondido, CA (US); Freeman Rose, Del Mar, CA (US); Marc Goldman, San Diego, CA (US)

(73) Assignee: QUASURAS, INC., Escondido, CA (US)

(*) Notice: Subject to any disclaimer, the term of this patent is extended or adjusted under 35 U.S.C. 154(b) by 11 days.

(21) Appl. No.: 17/968,599

(22) Filed: Oct. 18, 2022

(65) Prior Publication Data

US 2023/0044763 A1 Feb. 9, 2023

Related U.S. Application Data

(62) Division of application No. 16/028,256, filed on Jul. 5, 2018, now Pat. No. 11,504,472.

(Continued)

(51) Int. Cl.
*A61M 5/172* (2006.01)
*A61M 5/142* (2006.01)
(Continued)

(52) U.S. Cl.
CPC ...... *A61M 5/1723* (2013.01); *A61M 5/14224* (2013.01); *A61M 5/14248* (2013.01); *A61M 5/145* (2013.01); *A61M 5/1452* (2013.01); *A61M 5/14526* (2013.01); *A61M 5/14586* (2013.01); *A61M 5/14593* (2013.01);
(Continued)

(58) Field of Classification Search
CPC .......... A61M 5/14224; A61M 5/14248; A61M 5/145; A61M 5/1452; A61M 5/14586; A61M 5/16804; A61M 5/16809; A61M 5/16881; A61M 5/14526; A61M 5/14593; A61M 5/148–155; A61M 5/16877; A61M 2005/14264; A61M 2005/14533; A61M 2039/2433; A61M 2039/244; A61M 2039/2446; A61M 2039/246;
(Continued)

(56) References Cited

U.S. PATENT DOCUMENTS 4,142,523 A * 3/1979 Stegeman ............. A61M 5/165
                                              604/245
4,236,880 A 12/1980 Archibald
(Continued)

FOREIGN PATENT DOCUMENTS

| EP | 3165247 | 5/2017 |
|----|---------|--------|
| GB | 2548131 | 9/2017 |

(Continued)

OTHER PUBLICATIONS

Final Office Action dated: Aug. 18, 2023 in U.S. Appl. No. 17/111,396, filed Dec. 3, 2020 and published as: US2021/0170095 on Jun. 10, 2021.

(Continued)

*Primary Examiner* — Scott J Medway
*Assistant Examiner* — Anh Bui
(74) *Attorney, Agent, or Firm* — SCHMEISER, OLSEN & WATTS LLP

(57) ABSTRACT

Methods and devices for accurately pumping small quantities of liquid to a patient with a broad range of flow and low cost.

11 Claims, 18 Drawing Sheets

Related U.S. Application Data

(60) Provisional application No. 62/529,086, filed on Jul. 6, 2017.

(51) Int. Cl.
  *A61M 5/145* (2006.01)
  *A61M 5/168* (2006.01)
  *A61M 39/24* (2006.01)
  *A61M 5/315* (2006.01)

(52) U.S. Cl.
  CPC .... *A61M 5/16804* (2013.01); *A61M 5/16809* (2013.01); *A61M 5/16877* (2013.01); *A61M 5/16881* (2013.01); *A61M 39/24* (2013.01); *A61M 2005/14252* (2013.01); *A61M 2005/14264* (2013.01); *A61M 2005/14533* (2013.01); *A61M 5/31513* (2013.01); *A61M 2039/2433* (2013.01); *A61M 2039/244* (2013.01); *A61M 2039/2446* (2013.01); *A61M 2039/246* (2013.01); *A61M 2205/3331* (2013.01)

(58) Field of Classification Search
  CPC ..... A61M 2039/2406–242; A61M 2205/3331; A61M 39/24
  See application file for complete search history.

(56) References Cited

U.S. PATENT DOCUMENTS

| | | | |
|---|---|---|---|
| 4,594,058 A * | 6/1986 | Fischell | A61M 5/14224 92/99 |
| RE32,303 E | 12/1986 | Lasker et al. | |
| 4,954,046 A | 9/1990 | Irvin et al. | |
| 5,165,873 A | 11/1992 | Meijer | |
| 5,399,168 A | 3/1995 | Wadsworth et al. | |
| 5,499,909 A | 3/1996 | Yamada et al. | |
| 5,573,515 A | 11/1996 | Wilson et al. | |
| 6,077,246 A | 6/2000 | Kullas et al. | |
| 6,186,682 B1 * | 2/2001 | Ishiyama | G06F 3/1247 400/70 |
| 6,186,982 B1 | 2/2001 | Gross et al. | |
| 6,406,458 B1 | 6/2002 | Tillander | |
| 6,416,293 B1 * | 7/2002 | Bouchard | F04B 43/107 417/313 |
| 6,620,138 B1 | 9/2003 | Marrgi et al. | |
| 6,669,669 B2 | 12/2003 | Flaherty et al. | |
| 6,742,992 B2 | 6/2004 | Davis | |
| 7,500,962 B2 | 3/2009 | Childers et al. | |
| 7,658,734 B2 | 2/2010 | Adair et al. | |
| 7,789,849 B2 | 9/2010 | Busby et al. | |
| 8,029,460 B2 | 10/2011 | Rush et al. | |
| 8,056,582 B2 | 11/2011 | DiPerna | |
| 8,167,581 B2 | 5/2012 | Schneeberger et al. | |
| 8,298,184 B2 | 10/2012 | DiPerna et al. | |
| 8,408,421 B2 | 4/2013 | DiPerna | |
| 8,425,493 B2 | 4/2013 | Lord et al. | |
| 8,448,824 B2 | 5/2013 | DiPerna | |
| 8,545,440 B2 | 10/2013 | Patrick et al. | |
| 8,573,027 B2 | 11/2013 | Rosinko et al. | |
| 8,905,731 B2 | 12/2014 | Baron | |
| 8,926,561 B2 | 1/2015 | Verhoef et al. | |
| 8,939,928 B2 | 1/2015 | Savoie et al. | |
| 8,986,253 B2 | 3/2015 | DiPerna | |
| 9,211,377 B2 | 12/2015 | DiPerna et al. | |
| 9,250,106 B2 | 2/2016 | Rosinko et al. | |
| 9,295,779 B2 | 3/2016 | Kamen et al. | |
| 9,675,756 B2 | 6/2017 | Kamen et al. | |
| 10,010,674 B2 | 7/2018 | Rosinko et al. | |
| 10,213,546 B2 | 2/2019 | Anderson et al. | |
| 10,279,106 B1 | 5/2019 | Cook et al. | |
| 11,464,899 B2 | 10/2022 | Searle et al. | |
| 2002/0004643 A1 | 1/2002 | Carmel et al. | |
| 2003/0086799 A1 | 5/2003 | Falk et al. | |
| 2004/0034331 A1 | 2/2004 | Toman et al. | |
| 2004/0257413 A1 | 12/2004 | Anderson et al. | |
| 2005/0038386 A1 | 2/2005 | Fago et al. | |
| 2005/0119611 A1 | 6/2005 | Marano-Ford et al. | |
| 2005/0214129 A1 | 9/2005 | Greene et al. | |
| 2008/0051716 A1 | 2/2008 | Stutz | |
| 2008/0092969 A1 | 4/2008 | DiPerna | |
| 2010/0145303 A1 | 6/2010 | Yodfat et al. | |
| 2010/0185322 A1 | 7/2010 | Bylsma et al. | |
| 2010/0198182 A1 | 8/2010 | Lanigan et al. | |
| 2010/0232992 A1 | 9/2010 | Gray | |
| 2011/0021993 A1 | 1/2011 | Bar-Haim et al. | |
| 2011/0118694 A1 | 5/2011 | Yodfat et al. | |
| 2011/0186177 A1 | 8/2011 | Lanier, Jr. et al. | |
| 2011/0196304 A1 | 8/2011 | Kramer et al. | |
| 2013/0055889 A1 | 3/2013 | Herz et al. | |
| 2013/0101910 A1 | 4/2013 | Barton | |
| 2013/0150824 A1 | 6/2013 | Estes et al. | |
| 2013/0237947 A1 | 9/2013 | Amirouche et al. | |
| 2014/0134561 A1 | 5/2014 | Smith et al. | |
| 2014/0228762 A1 | 8/2014 | Capone et al. | |
| 2014/0276422 A1 | 9/2014 | Reilly et al. | |
| 2014/0378903 A1 | 12/2014 | Quinlan | |
| 2014/0378943 A1 | 12/2014 | Geipel | |
| 2015/0085179 A1 | 3/2015 | Huegten | |
| 2015/0273201 A1 | 10/2015 | Tallarida et al. | |
| 2015/0290445 A1 | 10/2015 | Powers et al. | |
| 2015/0343143 A1 | 12/2015 | Estes et al. | |
| 2015/0352296 A1 | 12/2015 | Yodfat et al. | |
| 2016/0038675 A1 | 2/2016 | Estes et al. | |
| 2016/0120751 A1 | 5/2016 | Mounce et al. | |
| 2016/0129178 A1 | 5/2016 | Askarinya et al. | |
| 2016/0151560 A1 | 6/2016 | Toro et al. | |
| 2016/0361489 A1 | 12/2016 | Di Perna | |
| 2017/0128709 A1 | 5/2017 | Chen | |
| 2017/0203030 A1 | 7/2017 | Brewer et al. | |
| 2017/0216520 A1 | 8/2017 | Kamen et al. | |
| 2017/0246380 A1 | 8/2017 | Rosinko et al. | |
| 2017/0286638 A1 | 10/2017 | Searle et al. | |
| 2018/0001000 A1 | 1/2018 | Herwig et al. | |
| 2018/0085521 A1 | 3/2018 | Allis et al. | |
| 2018/0369481 A1 | 12/2018 | Pedersen et al. | |
| 2019/0009023 A1 | 1/2019 | Di Perna et al. | |
| 2019/0143044 A1 | 5/2019 | Paramanandam et al. | |
| 2019/0355481 A1 | 11/2019 | Lamb et al. | |
| 2020/0030529 A1 | 1/2020 | Di Perna et al. | |
| 2020/0214625 A1 | 6/2020 | Hooven et al. | |
| 2021/0042730 A1 | 2/2021 | Lee | |
| 2021/0084700 A1 | 3/2021 | Daniels et al. | |
| 2021/0134184 A1 | 5/2021 | Baker et al. | |
| 2021/0170095 A1 | 6/2021 | DiPerna et al. | |
| 2022/0092960 A1 | 3/2022 | Arumugam et al. | |
| 2022/0101992 A1 | 3/2022 | Porter et al. | |
| 2023/0108800 A1 | 4/2023 | Neese et al. | |

FOREIGN PATENT DOCUMENTS

| | | |
|---|---|---|
| WO | WO 15/134526 | 9/2015 |
| WO | WO 17/194074 | 11/2017 |
| WO | WO 19/010324 | 1/2019 |
| WO | WO 19/079474 | 4/2019 |
| WO | WO 21/113537 | 6/2021 |
| WO | WO 21/113538 | 6/2021 |
| WO | WO 22/076337 | 4/2022 |

OTHER PUBLICATIONS

International Search Report and Written Opinion dated: Oct. 18, 2018 in International Application No. PCT/US2018/40944, filed: Jul. 5, 2018 and published as: WO/2019/010324 on Jan. 10, 2019.
International Search Report and Written Opinion dated: Jul. 31, 2015 in International Application No. PCT/US2015/18525 filed: Mar. 3, 2015 and published as: WO/2015/134526 on: Sep. 11, 2015.
International Search Report and Written Opinion dated: Oct. 4, 2019 in International Application No. PCT/US2019/43146 filed: Jul. 24, 2019.
Office Action dated: Jan. 2, 2020 in U.S. Appl. No. 15/122,132, filed Aug. 26, 2016 and published as: 2016/0361489 on Dec. 15, 2016.

(56) References Cited

OTHER PUBLICATIONS

Final Office Action dated: Jun. 26, 2020 in U.S. Appl. No. 15/122,132, filed Aug. 26, 2016 and published as: 2016/0361489 on Dec. 15, 2016.
Invitation to Pay Additional Fees dated: Feb. 23, 2021 in International Application No. PCT/US2020/63152 filed: Dec. 3, 2020.
International Preliminary Report on Patentability dated: Jan. 26, 2021 in International Application No. PCT/US2019/43146 filed: Jul. 24, 2019.
Supplementary European Search Report dated: Mar. 12, 2021 in European Patent Application No. EP 18828123.2 filed: Jul. 5, 2018.
International Search Report and Written Opinion dated Feb. 26, 2021 in International Patent Application No. PCT/US2020/63151 filed: Dec. 3, 2020.
International Preliminary Report on Patentability dated May 17, 2022 in International Patent Application No. PCT/US2020/63151 filed: Dec. 3, 2020.
Corrected Notice of Allowance dated: Jun. 28, 2021 in U.S. Appl. No. 15/122,132, filed Aug. 26, 2016 and published as: 2016/0361489 on: Dec. 15, 2016.
Notice of Allowance dated: Jun. 1, 2021 in U.S. Appl. No. 15/122,132, filed Aug. 26, 2016 and published as: 2016/0361489 on: Dec. 15, 2016.
Non-Final Office Action dated: Nov. 3, 2022 in U.S. Appl. No. 17/166,833, filed Feb. 3, 2021 and published as: US2021/0249113 on Aug. 12, 2022.
Non-Final Office Action dated: Dec. 1, 2022 in U.S. Appl. No. 17/111,396, filed Dec. 3, 2020 and published as: US2021/0170095 on Jun. 10, 2021.
Final Office Action dated: Jan. 23, 2024 in U.S. Appl. No. 17/111,396, filed Dec. 3, 2020 and published as: US2021/0170095 on Jun. 10, 2021.
Extended European Search Report dated Nov. 21, 2023 in European Patent Application No: 20896925.3 filed: Dec. 3, 2020.
Supplemental European Search Report dated: Jan. 24, 2024 in European Patent Application No. 20896021.1 filed: Dec. 3, 2020.
Non-Final Office Action dated: Apr. 26, 2023 in U.S. Appl. No. 17/111,402, filed Dec. 3, 2020 and published as: US/2021/0170094 on Jun. 10, 2021.
Final Office Action dated: Apr. 14, 2023 in U.S. Appl. No. 17/111,396, filed Dec. 3, 2020 and published as: US2021/0170095 on Jun. 10, 2021.
Final Office Action dated: Mar. 21, 2023 in U.S. Appl. No. 17/166,833, filed Feb. 3, 2021 and published as: US2021/0249113 on Aug. 12, 2022.
International Search Report and Written Opinion dated Feb. 23, 2023 in International Patent Application No. PCT/US2022/045065 filed: Sep. 28, 2022 and published as: WO/2023/055819 on: Apr. 6, 2023.
Final Office Action dated: Oct. 19, 2023 in U.S. Appl. No. 17/111,402, filed Dec. 3, 2020 and published as: US/2021/0170094 on Jun. 10, 2021.
Non-Final Office Action dated: Jul. 5, 2024 in U.S. Appl. No. 17/111,402, filed Dec. 3, 2020 and published as: US/2021/0170094 on Jun. 10, 2021.
Non-Final Office Action dated: Jun. 6, 2024 in U.S. Appl. No. 17/111,396, filed Dec. 3, 2020 and published as: US2021/0170095 on Jun. 10, 2021.
Non-Final Office Action dated: Jul. 3, 2024 in U.S. Appl. No. 18/485,156, filed Oct. 11, 2023 and published as: US2024/0038359 on Feb. 1, 2024.
Final Office Action dated: Nov. 6, 2024 in U.S. Appl. No. 17/111,402, filed Dec. 3, 2020 and published as: US 2021-0170094 A1 on: Jun. 10, 2021.
Final Office Action dated: Oct. 24, 2024 in U.S. Appl. No. 17/111,396, filed Dec. 3, 2020 and published as: US 2021-0170095 A1 on: Jun. 10, 2021.

* cited by examiner

MEDICAL PUMP WITH FLOW CONTROL

RELATED APPLICATIONS

The present application is a divisional of U.S. patent application Ser. No. 16/028,256, filed Jul. 5, 2018, by Paul M. DIPERNA et al. titled "MEDICAL PUMP WITH FLOW CONTROL", which claims priority from U.S. Provisional Patent Application Ser. No. 62/529,086, filed on Jul. 6, 2017, by Paul M. DiPerna, entitled "VARIABLE FLOW ORIFICE WITH DYNAMIC CONTROL FEEDBACK", each of which is incorporated by reference herein in its entirety.

BACKGROUND

Moving small quantities of fluid in ambulatory devices is challenging due to the limited feedback on the fluid that is received after the motors have turned. When pushing fluid with a syringe type of disposable pump system, for instance, although the motion of the motor can be determined, friction between a rubber plunger and a barrel of a syringe may create problems where the entire drive unit tightens but the plunger does not move thereby no fluid is delivered to the patient. This effect, commonly called stiction, can be minimized with silicon oil. However, this oil may infuse into patients such as people with diabetes. Such diabetes patients are continuously on such pumps creating unknown potential health issues. In addition, the use of such oil has been shown in some studies to compromise the stability and storage life of insulin. Lead screws and gearboxes of such plunger based pumps must have clearances between mating parts creating backlash that contributes to variability in the system as it attempts to consistently deliver liquid down to the microliter level even though the pump could be in very different positions due to the motion of the person. Mini peristaltic motors have been developed as well but the variability in the flexible tubing and affects from changes in ambient conditions may also make accurate microfluidic delivery difficult. Although a reciprocating piston pump was developed by DiPerna et al. as discussed in U.S. Pat. No. 8,298,184 to minimize these effects with a small bore syringe that refills from time to time, the cost of this approach has been high making commercial viability difficult.

In high liquid volume pumping applications, check valves open at its cracking pressure, deliver fluid, then close when pressure is reduced are often used. Dispensing a minimum amount of liquid required for micro delivery has been a persistent problem within the industry when using such standard check valves because the minimum amount of liquid delivered upon achieving the cracking pressure may be too much volume for micro delivery applications. Peristaltic type of delivery, pressing on tubing and pulling fluid from the container when the tubing returns to round and alternately pushing it towards the patient has also been used but variability in tubing both in manufacturing and during delivery has plagued the accuracy of this approach.

Small orifice restrictors often made of glass or rubies are often used where the fluid pressure is kept relatively constant and the small orifice controls the flow rate of the liquid. There is a linear relationship between the pressure and the flow rate making the control of flow relatively straightforward. Controlling pressure however is a difficult task as is the case of rubber balloon devices where the rubber contracts with variable pressure. Also these small orifice restrictors are expensive and may be plagued with blockage from particulate and air bubbles. What have been needed are methods and devices for accurately pumping microliter size quantities of liquid to a patient with a broad range of flow rate and low cost.

SUMMARY

Some embodiments of a medical pump for delivering fluid to a patient may include a pump cavity which is surrounded by a rigid wall and which includes a diaphragm opening. A diaphragm may be disposed over and sealed to the diaphragm opening of the pump cavity. The medical pump may also include a pump chamber defined by an inside surface of the rigid wall of the pump cavity and an inside surface of the diaphragm which disposed over and sealed to the pump cavity. A pressure actuator may include a piston with a distal end that is operatively coupled to the diaphragm. In addition an inlet conduit may also be disposed in fluid communication with the pump chamber. A check valve may be operatively coupled to the inlet conduit and may also be oriented to allow a flow of liquid to the pump chamber but prevent a flow of liquid from the pump chamber back towards the check valve. An outlet conduit may be disposed in fluid communication with the pump chamber and an outlet port disposed in fluid communication with the outlet conduit. The medical pump may optionally further include a flow control valve which is operatively coupled to the outlet conduit between the pump chamber and the outlet port. Embodiments of the flow control valve may further include a rigid base having a top surface with an upstream orifice and a downstream orifice and a distensible membrane secured to the top surface of the rigid base in sealed relation relative to the upstream orifice and the downstream orifice so as to be in close approximation with the top surface of the rigid base forming a sealed distensible channel between the upstream and downstream orifices that is normally closed.

Some embodiments of a method of pumping a liquid from a medical pump to a patient may include actuating a motor of a pressure actuator and advancing a piston of the pressure actuator into a diaphragm of a pump chamber of the medical pump such that an inside surface of the diaphragm intrudes into the pump chamber thereby increasing an internal pressure within an interior volume of the pump chamber and expelling liquid from the pump chamber through an outlet conduit. The method may also include flowing the liquid expelled from the pump chamber through the outlet conduit and into a distensible channel of a flow control valve which is normally closed. The flowing of the liquid into the distensible channel results in stretching a distensible membrane of the flow control valve and expanding the distensible channel to allow a flow of the liquid through the flow control valve and out of an outlet port of the outlet conduit.

Some embodiments of a medical pump for delivering fluid to a patient may include a pump cavity which is surrounded by a rigid wall, the pump cavity further including a diaphragm opening. A diaphragm may be disposed over and sealed to the diaphragm opening of the pump cavity forming a pump chamber which is defined by an inside surface of the rigid wall of the pump cavity and an inside surface of the diaphragm which disposed over and sealed to the pump cavity. A pressure actuator may include a piston, for example, with a distal end that is operatively coupled to the diaphragm. The medical pump may further include an outlet conduit which is in fluid communication with the pump chamber and an outlet port which is in fluid communication with the outlet conduit. A flow control valve may be operatively coupled to the outlet conduit between the pump chamber and the outlet port, the flow control valve further including a rigid base having a top surface with an upstream orifice and a downstream orifice and a distensible membrane secured to the top surface of the rigid base in sealed relation relative to the upstream orifice and the downstream orifice so as to be in close approximation with the top surface of the rigid base forming a sealed distensible channel between the upstream and downstream orifices that is normally closed.

Some embodiments of a method of pumping a liquid from a medical pump to a patient may include actuating a motor of a pressure actuator and advancing a piston of the pressure actuator into a diaphragm of a pump chamber of the medical pump such that an inside surface of the diaphragm extends into the pump chamber and intrudes into the interior volume of the pump chamber so as to increase a pressure within an interior volume of the pump chamber and expel liquid from the pump chamber into an outlet conduit. The method may also include flowing the liquid expelled from the pump chamber into the outlet conduit and into a distensible channel of a flow control valve which is normally closed. The flowing of the liquid into the distensible channel results in stretching a distensible membrane of the flow control valve and expanding the distensible channel to allow a flow of the liquid through the flow control valve and out of an outlet port of the outlet conduit.

Some embodiments of a method of welding a distensible membrane to a rigid base of a pump cavity may include positioning the distensible membrane onto a top surface of the rigid base such that an inside surface of the distensible membrane is in contact with the top surface of the rigid base. Thereafter, a layer of rigid material, that may optionally include a rigid material, may be positioned onto an outside surface of the distensible membrane over an area between the distensible membrane and rigid base to be welded. The method may further include applying pressure to the distensible membrane in a direction towards the rigid base thereby approximating the inside surface of the distensible membrane with the top surface of the rigid base and transmitting electromagnetic energy through the layer of rigid material and onto the distensible membrane until the distensible membrane and rigid base melt and form a fluid tight weld zone. In some cases, the layer of material may be positioned so as to provide a predetermined minimum pressure on the distensible membrane prior to welding so as to adjust the pressure required to open the distensible membrane and thereby the cracking pressure and minimal dispensed volume of liquid.

Certain embodiments are described further in the following description, examples, claims and drawings. These features of embodiments will become more apparent from the following detailed description when taken in conjunction with the accompanying exemplary drawings.

The drawings are intended to illustrate certain exemplary embodiments and are not limiting. For clarity and ease of illustration, the drawings may not be made to scale and, in some instances, various aspects may be shown exaggerated or enlarged to facilitate an understanding of particular embodiments.

DETAILED DESCRIPTION

In some cases, medical pump embodiments discussed herein may include the use of a flow control valve that combines the functions of a check valve opened by pressure applied to the check valve and a flow restrictor where a flow rate may be determined by the liquid pressure differential across each of the sides of a restriction caused by the flow restrictor. Since the flow restrictor may be flexible in this case, the flow rate may also be determined by the elastic properties of the material used to create the flow restrictor. By simply creating air pressure against a flexible liquid chamber filled with a fluid and measuring the air pressure response to the change in liquid volume, flow feedback may be achieved. Such a device and process may have significant safety and cost advantages over the present art since the control may easily be done by measuring and controlling an air pressure response to a pressure influence through a flow restrictor/check valve in the liquid chamber. The air chamber may optionally be open to the atmosphere to provide altitude feedback and replace a volume of liquid that has been displaced. By combining these two techniques of simple pressure pumping and using low cost materials, such a configuration may have significant cost and performance advantages over the present art.

Figure 1:
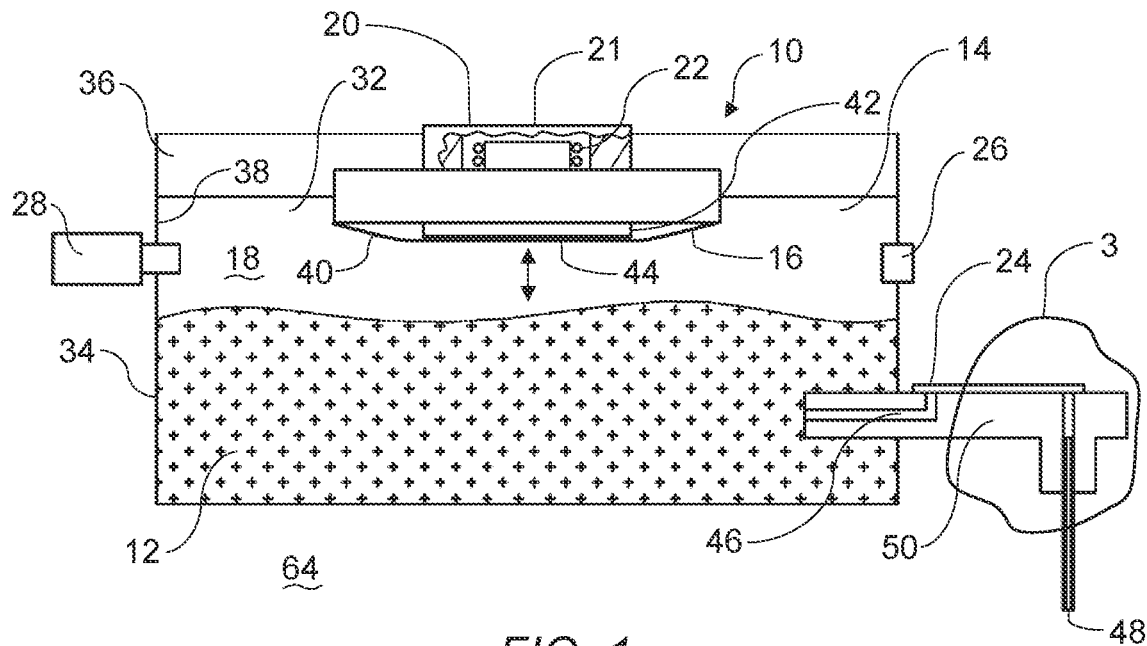
FIG. 1 is a schematic representation in elevation of a medical pump embodiment.

Methods of creating low cost medical pump embodiments 10 are discussed herein that may allow, for instance, a bioactive material such as a medicament or any other desired liquid 12, to be delivered to a patient with precision. In general, the medical pump embodiments discussed herein may be used to administer liquids to a patient such as insulin, antibiotics, saline, dextrose or any other useful liquid used to treat or otherwise assist a patient. Any of the medical pump embodiments discussed herein may be adapted for use as portable insulin pumps such as patch pumps or the like for use by diabetic patients. For some embodiments, a rigid liquid pump chamber 14 with a flexible film diaphragm 16 on a least one side of the fluid is envisioned having an air space of a pump chamber 18 between the liquid chamber and the flexible film as shown in FIG. 1. Operating a motor 21 of a pressure actuator 20 such as by displacing an airtight diaphragm 16 of a speaker, as an example, may be used to create this air pressure.

The amount of air displacement may be varied as a function of the voltage that is applied to the coil 22 of the speaker 20. As this liquid flows under pressure though the check valve/variable flow restrictor which is exemplified in the embodiment of FIG. 1 as a flow control valve 24, the quantity of liquid displaced may be replaced by the reduction in the air and thereby the pressure. For short bursts of air pressure the check valve may be used to displace a very small quantity of liquid. In some cases, the amount of liquid that is delivered may be selected by the magnitude of displacement of the speaker 20 and the amount of time the speaker is displaced. The air pressure may be measured with a pressure sensor 26 which is in fluid communication with the liquid chamber 18 and using Boyles Law the quantity of liquid displaced may be calculated. Upon reaching a point of sufficient or desired liquid displacement, power to the coil 22 of the speaker 20 may be terminated and the system returns to equilibrium.

To replace the displaced liquid 12 and bring the air pressure back to room level with outside ambient air pressure, a standard currently available flexible check valve 28 may be added with a known cracking pressure. When the air pressure become sufficiently low, this check valve 28 will open and allow air to return into the pump chamber 18 replacing the liquid 12 that has been displaced. Actuating the coil 22 of the speaker in reverse may be used to create a further level of vacuum to controllably let air in so this doesn't occur during the liquid flow part of the cycle.

Figure 25:
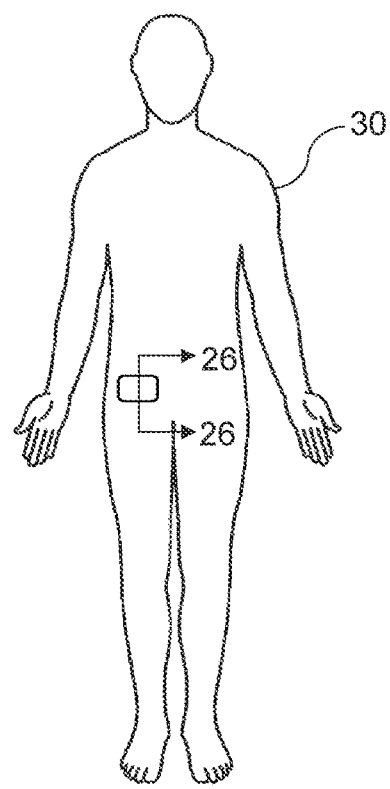
FIG. 25 is a schematic view of a human patient with the medical pump embodiment of FIG. 13 disposed in operative communication with tissue of the patient.
Figure 26:
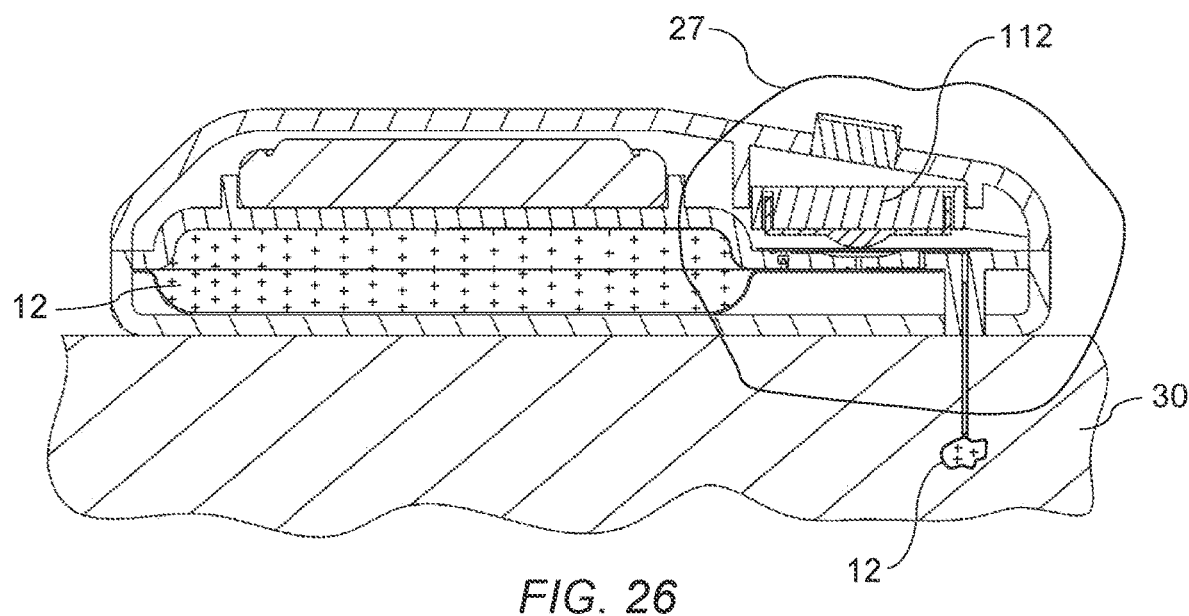
FIG. 26 is an enlarged view in section of the medical pump of FIG. 25 taken along lines 26-26 of FIG. 25.

Some embodiments of a medical pump as shown in FIG. 1 for delivering fluid 12 to a patient 30 (see FIG. 25) may include a pump cavity 32 which is surrounded by a rigid wall 34, the pump cavity further including a diaphragm opening 36. The diaphragm 16 may be disposed over and sealed to the diaphragm opening 36 of the pump cavity forming the pump chamber 18 which is defined by an inside surface 38 of the rigid wall 34 of the pump cavity 18 and an inside surface 40 of the diaphragm 16 which disposed over and sealed to the pump cavity. The pressure actuator 20 may include a piston 42 with a distal end 44 that is operatively coupled to the diaphragm 16. The medical pump 10 may further include an outlet conduit 46 which is in fluid communication with the pump chamber 18 and an outlet port 48 which is in fluid communication with the outlet conduit 46. The flow control valve 24 may be operatively coupled to the outlet conduit 46 between the pump chamber 18 and the outlet port 48, the flow control valve 24 further including a rigid base 50 having a top surface 52 with an upstream orifice 54 and a downstream orifice 56 and a distensible membrane 58 secured to the top surface 52 of the rigid base 50 in sealed relation relative to the upstream orifice 54 and the downstream orifice 56 so as to be in close approximation with the top surface 52 of the rigid base 50 forming a sealed distensible channel 60 between the upstream and downstream orifices 54, 56 that is normally closed.

Figure 2:
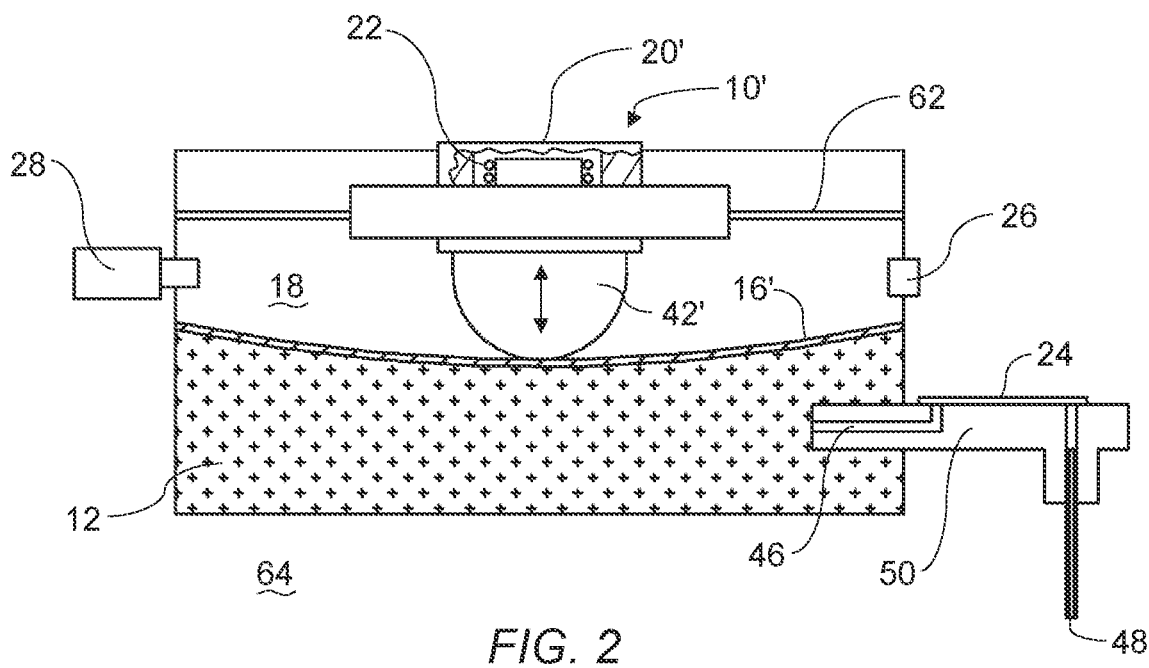
FIG. 2 is a schematic representation in elevation of a medical pump embodiment.

FIG. 2 illustrates a medical pump embodiment 10' that may have the same or similar features, dimensions and materials as those of the medical pump embodiment 10 of FIG. 1. However, pressure actuator 20' has a different configuration and the diaphragm 16' of the medical pump of FIG. 2 extends completely across the pump chamber 18 and makes direct contact with the liquid 12 disposed within the pump chamber. As such, there is no air cushion disposed between the liquid 12 and the diaphragm 16' and the piston 42' of the motor extends substantially to the level of the liquid 12 so as to effectively apply pressure directly onto the liquid through the diaphragm 16'. The flow control valve 24 of the medical pump 10' of FIG. 2 may be the same as the flow control valve 24 of the medical pump 10 of FIG. 1. The valve 28 in fluid communication with the air space disposed between the diaphragm 16' and a bulkhead 62 which seals the top opening 36 of the pump chamber and an ambient atmosphere 64 outside the medical pump structure. The bulkhead 62 also serves as a mount for the motor of the pressure actuator 20'. Such a valve 28 may be used to vent the air space in the pump chamber 18 and replace a volume of liquid 12 which has been dispensed from the pump chamber 18. The pressure sensor 26 is also in operative communication with the air space within the pump chamber 18 and may provide pressure measurements that are used to determine the amount of liquid 12 which has been dispensed from the pump chamber 18.

Figure 5:
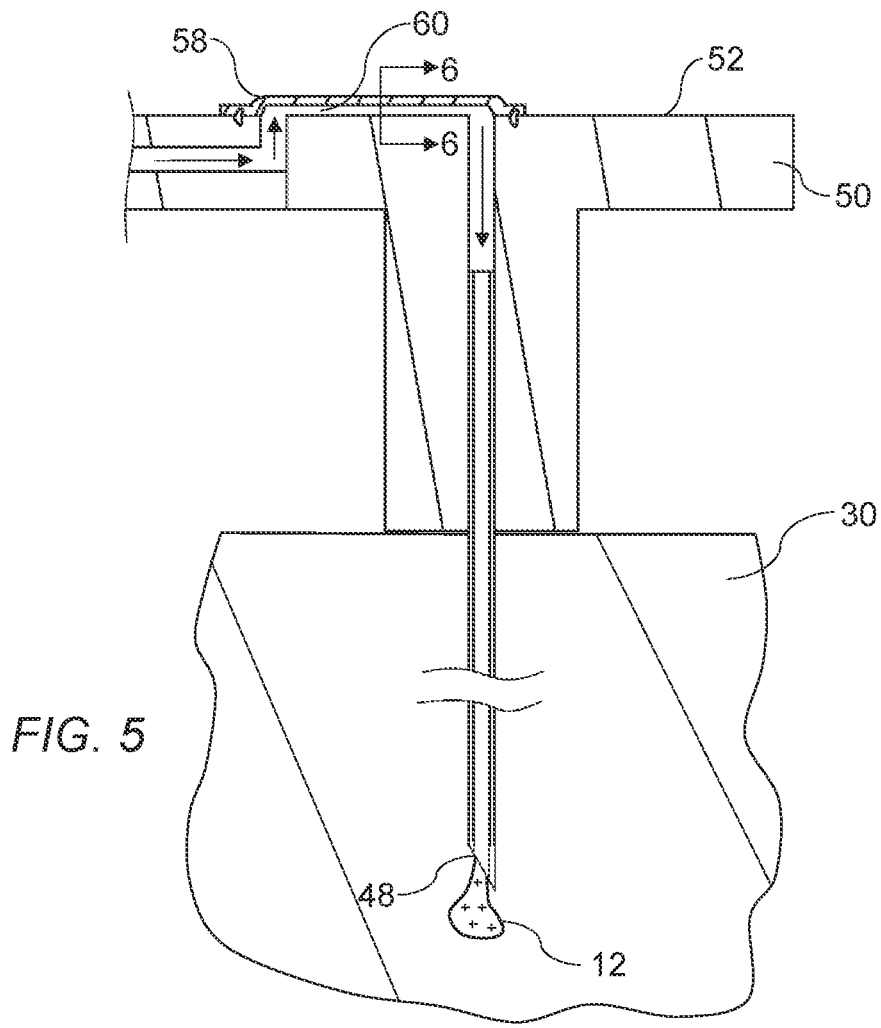
FIG. 5 is an enlarged view of the flow control valve portion of the medical pump of FIG. 1 with a needle tissue interface thereof engaged with tissue of a patient and the distensible channel of the flow control valve in an open state with liquid flowing therethrough and out of the inner lumen of the needle and into the tissue of the patient.
Figure 6:
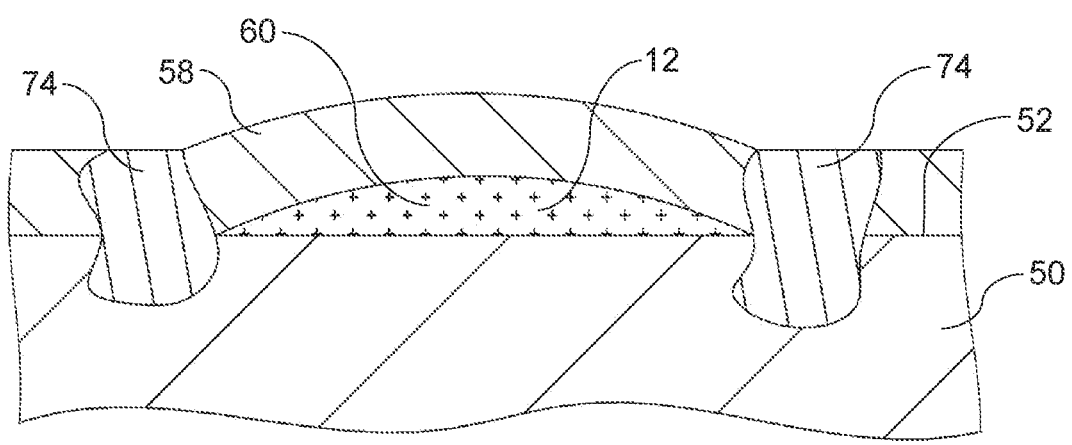
FIG. 6 is a section view of the distensible channel of the flow control valve of FIG. 5 taken along lines 6-6 of FIG. 5 with the distensible membrane distended and liquid flowing through the distensible channel.

Some embodiments of a method of pumping a liquid as shown in FIGS. 3-6 from the medical pump 10 as shown in FIG. 1 to a patient 30 may include actuating the motor of the pressure actuator 20 and advancing the piston 42 of the pressure actuator 20 into the diaphragm 16 of a pump chamber 18 of the medical pump 10 such that an inside surface 40 of the diaphragm 16 extends into the pump chamber 18 and intrudes into the interior volume of the pump chamber 18 so as to reduce an interior volume of the pump chamber, increase a pressure within the interior volume of the pump chamber 18 and expel liquid 12 from the pump chamber 18 into the outlet conduit 46. The method may also include flowing the liquid 12 expelled from the pump chamber 18 into the outlet conduit 46 and into the distensible channel 60 of a flow control valve 24 which is normally closed. The flowing of the liquid 12 into the distensible channel 60, as shown in FIG. 5, results in stretching a distensible membrane, as shown in FIG. 6, of the flow control valve 24 and expanding the distensible channel 60 to allow a flow of the liquid 12 through the flow control valve 24 and out of the outlet port 48 of the outlet conduit 46.

For some embodiments, a speaker, solenoid, piezo disk, motor, heating coil or any other suitable means may be used as a pressure actuator 20 to push on the air creating an increase in pressure within the interior volume to push on the air which then pushes on the liquid 12 so as to flow the liquid 12 through a distensible channel 60 of the flow control valve 20 and thereby open the distensible channel 60 of the flow control valve 20 and allow flow of liquid 12 through the distensible channel 60. For some embodiments, a quantity of pressure applied to the liquid 12 may be controlled by the displacement of the diaphragm 16 shown in FIG. 1 of the pressure actuator speaker 20 by varying the voltage applied to the coil 22 of the speaker. By measuring this pressure change the quantity of displacement and liquid flow may be calculated to allow for calibration of the displacing means and verification of proper liquid flow.

Such intermittent actuated liquid flow may be highly variable as a function of the characteristics of a distensible membrane 58 of the flow control valve 24 versus pressure and the pressure producing capabilities of the speaker 20. At slow flow rates the speaker may actuate slightly to raise the pressure a small amount before the liquid would flow through the distensible channel 60 of the flow control valve 24. At higher rates more motion of the speaker cone would allow the speaker to push more liquid 12 at a higher rate. By measuring the flow of liquid through measurement of a pressure response preprogramming the size of the cavity and other chambers, the entire system and quantity of liquid flow to a patient's body 30 may be calibrated. Further calibration may occur at point where the quantity of fluid 12 is known such as when the liquid pump chamber 18 is empty of liquid 12, full or when the known amount of liquid 12 is entered.

Another embodiment of returning air to the liquid pump chamber 18 may include use of a small orifice as the valve 28 that is always open between the air-filled portion of the liquid pump chamber 18 and the ambient atmosphere 64. A pressure change due to displacement of air may be measured and controllably decay over time. By using Poiseuille's law of flow through the small orifice 28, the amount of liquid displaced may be determined as a function of the pressure differential. This may then be subtracted from the pressure decay during flow to determine the air displacement and thereby the quantity of liquid that has been dispensed out of the pump to a patient's body 30. The small orifice 28 may be factory calibrated or by blocking the distensible channel 60 using an alternative pressure actuator so that the orifice can be calibrated with an actuation of the speaker 20 and subsequently subtracted from the flow to the liquid when the distensible channel 60 is opened. This calibration and redundancy phase is essential to creating a fail-safe product. For other embodiments, this alternative pressure actuator 20 such as a vibrator motor for example, may be added to a product for redundant control of flow and calibration of every new set that is added to the hardware.

For a medical pump embodiment 10 using a vibrator motor, each pressure wave generated by the motor 21 may send air and liquid out of the system, each return of the diaphragm 16 may thus return both to the system. In some cases, the characteristics of the check valve of the flow control valve 24 may prevent this return allowing the system to return only air to the liquid pump chamber 18. Therefore, the pressure sensor 26 may be measuring flow and air leakage for a known liquid pump chamber size and a known air volume. All that is needed is to characterize the speaker properties with a known volume of air. This can be done, for example with an empty liquid pump chamber 18 to verify calibration either at the factory or with a known empty liquid chamber as verification at the end of each usage or with a liquid pump chamber 18 with a known quantity of liquid 12.

Figure 7:
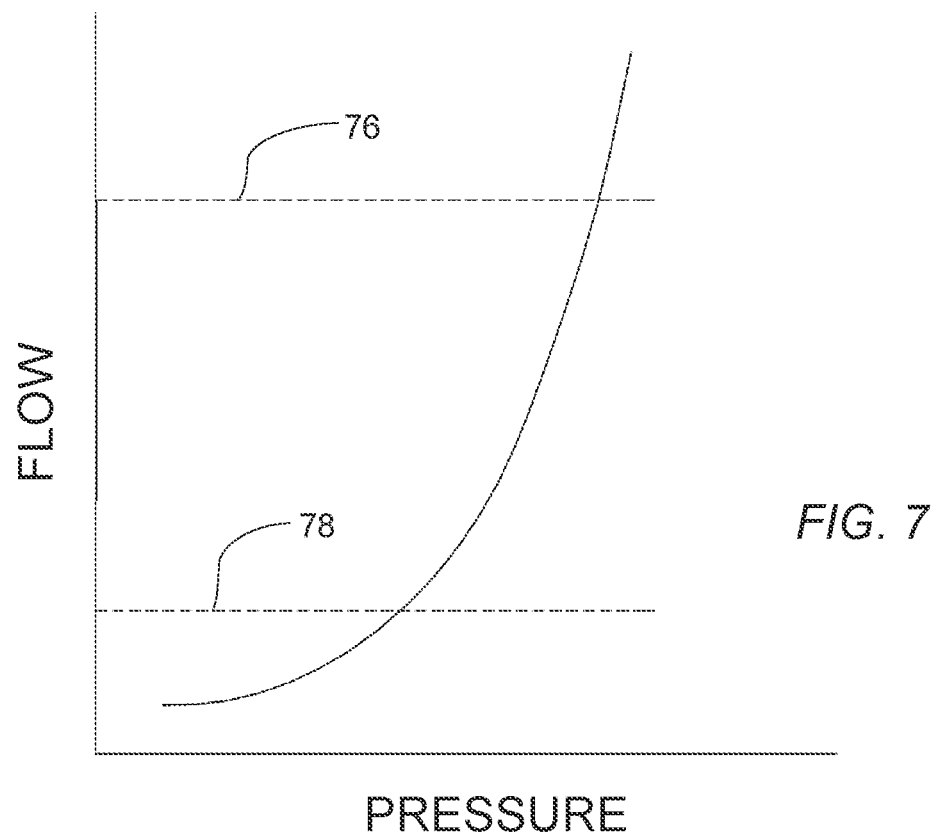
FIG. 7 is a graphical representation embodiment of flow characteristics of a flow control valve embodiment having a distensible channel formed from a distensible membrane and a rigid base.

Distensible membrane based flow control valve embodiments 24, as shown in FIGS. 3-6, may be closed under low pressure but flex as a function of the pressure applied to the distensible membrane 58 from within the distensible channel 60 allowing it open until the pressure is reduced by the passing of the fluid 12 or the reduction of air pressure. Furthermore, as the pressure increases the distensible channel 60 continues to open further allowing the flow rate to increase as shown in FIG. 7. FIG. 7 illustrates a relationship between pressure of liquid on an embodiment of the distensible channel 60 and resulting flow of liquid 12 through the distensible channel 60. A dashed line 76 is shown indicating a flow for a maximum bolus of fluid 12 and a dashed line 78 is shown indicating a level corresponding to a minimum safe leak level. Since the flow control valve 24 includes a distensible membrane 58 that may be made from a thin film of a polymer that is welded to plastic, such a configuration may offer significant size and cost advantages over alternative designs.

Figure 8:
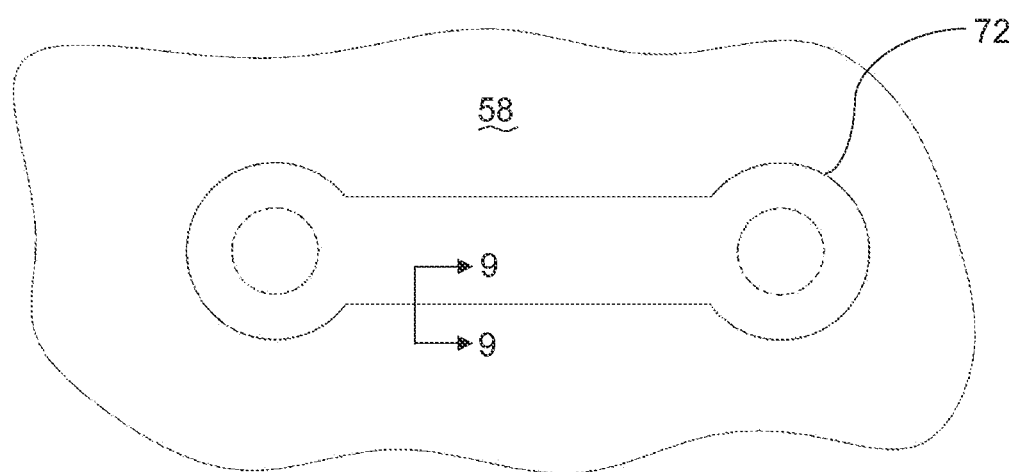
FIG. 8 is a broken away view of the distensible channel embodiment of the flow control valve of FIG. 3 showing a laser weld pattern on the distensible membrane and rigid base of the distensible channel.
Figure 9:
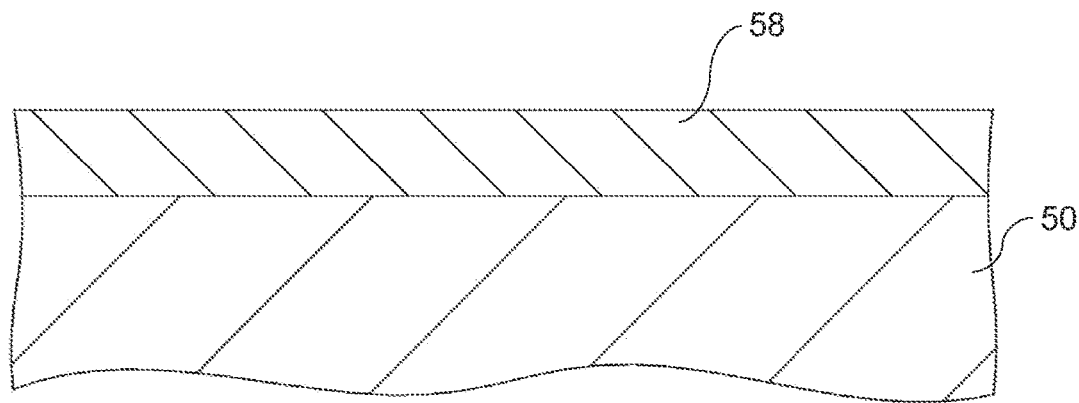
FIG. 9 is a section view of the distensible channel of FIG. 8 taken along lines 9-9 of FIG. 8.
Figure 10:
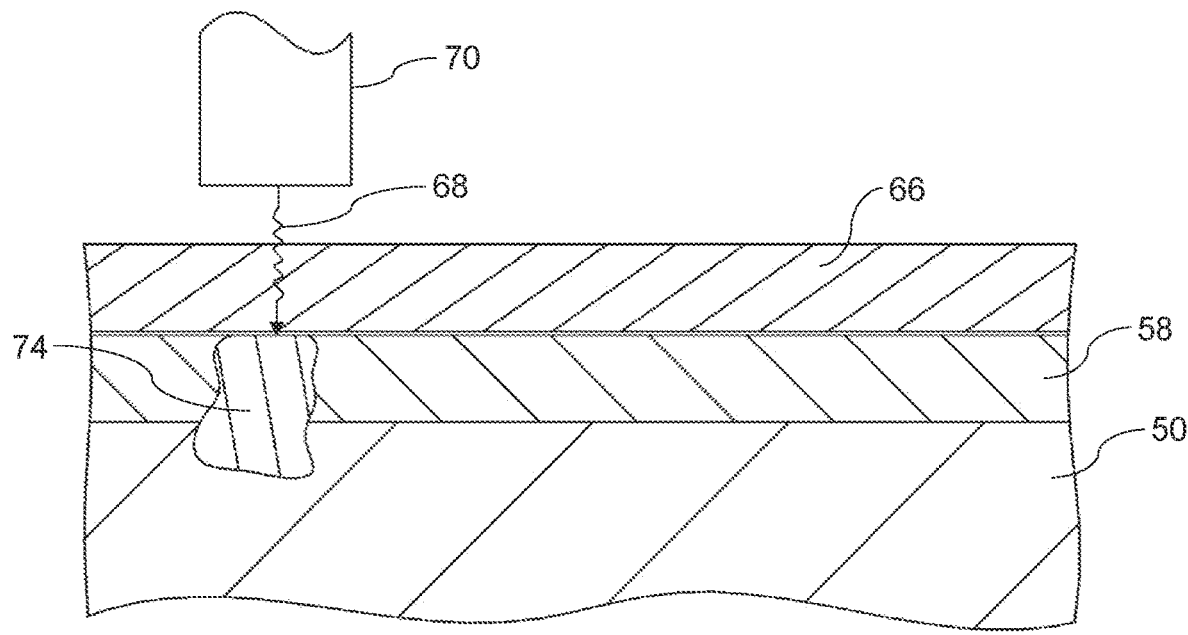
FIG. 10 is a section view of a distensible membrane embodiment disposed on a top surface of a rigid base embodiment and being held down by a piece layer of rigid material with laser energy being transmitted through the layer of rigid material to a weld zone between the distensible membrane and rigid base.

In some cases, an important part of heat welding of plastic, and laser welding technology as an example, may require that one part is impregnated with a colorant to allow the laser to warm the plastic. By pressing a clear plastic part against the light absorbing plastic part the energy of the laser may pass through the clear plastic and be absorbed by the dark plastic. Applying pressure to these plastic components with clear glass over the top, it will cause the plastic components to heat and bond. One application of this process may include joining plastic distensible membrane to plastic parts. Specifically, as shown in FIGS. 8-10, the distensible membrane film 58 may be pressed against a colored semi-rigid plastic or rigid plastic base 50 with clear glass plate 66. The laser energy 68 from a laser 70 passes through the glass plate 66 and distensible plastic membrane 58, hits the dark surface of the dark plastic rigid base 50 and heats the plastic. The combination of heat and expansion of the heated plastic against the distensible membrane 58 causes a thermal bond between the distensible membrane 58 and rigid dark plastic base. More importantly, this heating and subsequent cooling of both the dark part and distensible membrane 58 causes, for example, two close laser welded lines 72 to tighten the distensible membrane film 58 towards where the laser weld bonds 74 took place. If this occurs between two parallel laser weld bonding lines 72 this tightening may restrict flow along the distensible channel 60 created by this bonding as a function of the distance between the two bonds 74 creating the distensible flow channel 60. For some embodiments, the distensible membrane 58 may be secured to the rigid base 50 by other suitable methods including ultrasonic welding, solvent welding, adhesive bonding, or the like.

The tightened distensible membrane film 58 now works to block the majority of flow of liquid 12 attempting to traverse this distensible channel 60 created by joining the distensible membrane film 58 to the rigid plastic base 50. As the liquid pressure is increased the elastic properties of the distensible membrane film 58 begin to stretch allowing liquid flow to occur. The liquid flow through the distensible channel 60 is not linear as a function of pressure as is classically done with orifice flow through a rigid small channel, but instead may be exponential allowing a relatively small amount of pressure to flow considerable liquid 12. At low pressure such as the pressure due to the movement of the system on the patient's body 30 for instance it fails to create sufficient pressure to open and the small head height differential between the liquid 12 and the flow control valve 24 and the distensible membrane film 58 is able to resist pressure and open. By adding a means of creating pressure on the liquid 12, the pressure within the liquid pump chamber 18 may be controllably varied to achieve a desired liquid flow rate or an aliquot of fluid 12 requested by varying the amount of pressure and the time the pressure is applied.

Such a medical pump embodiment may provide a low cost, easy to manufacture combination of a check valve and variable flow and cracking volume orifice to the flow of liquid 12. By varying the pressure on the liquid 12 the amount of liquid 12 passing through the distensible channel 60 versus time can be varied. Feedback of the liquid movement occurs by measuring the pressure. By knowing the air volume and pressure created along with Boyles law of flow, a predictable quantity of liquid 12 may be dispensed.

Figure 11:
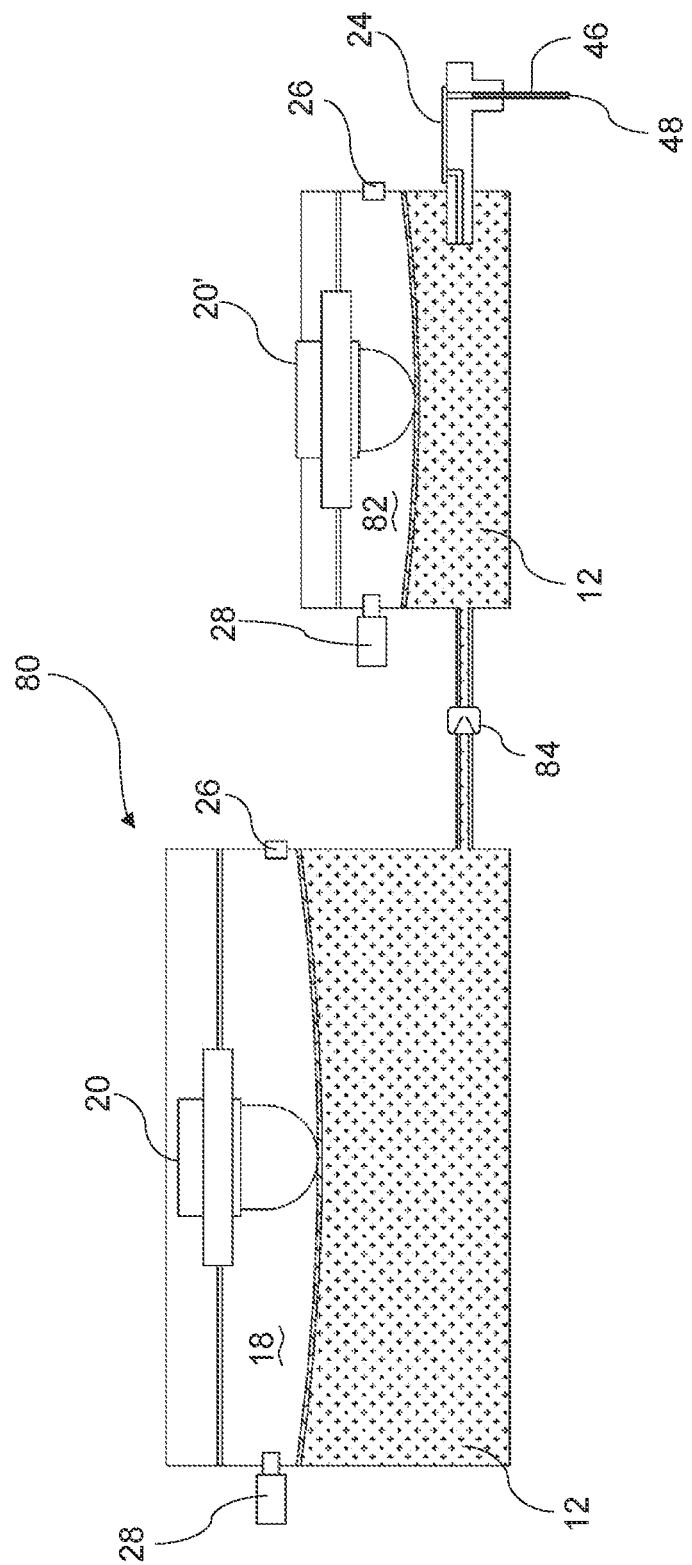
FIG. 11 is a medical pump embodiment including a first pump chamber and first pressure actuator, a second pump chamber and second pump actuator, and a flow control valve.

Another medical pump embodiment 80 and/or measure of safety may include use of a second liquid pump chamber 82, much smaller than the pump chamber 18, that is filled between the liquid chamber and the patient as shown in FIG. 11. The smaller second liquid pump chamber 82 may then be emptied by actuation of a second pressure actuator 20' similar to the first pressure actuator 20, which may include, for example a second speaker. Upon filling the second liquid pump chamber 82 through a check valve 84, the second pressure actuator 20' may push the liquid 12 forward through yet another flow control valve 24 with the distensible channel 60 to the patient 30 as shown in FIG. 5. In some cases, the check valve 84 may include either a passive check valve or active check valve that may be controlled by the transmission of a signal or energy source to the check valve. Failure of the second flow control valve 24 may only expose the patient 30 to the small quantity of liquid 12 versus the liquid contents of the entire liquid chamber 18. This would, for example, allow for much higher pressure in the delivery of the liquids 12 may allow the liquid to overcome and flow through an obstruction in the outlet conduit 46 which may include a cannula that is kinked, body fluid pressure, capillary effects in small bore tubing and tissues against the end of the cannula.

Figure 3:
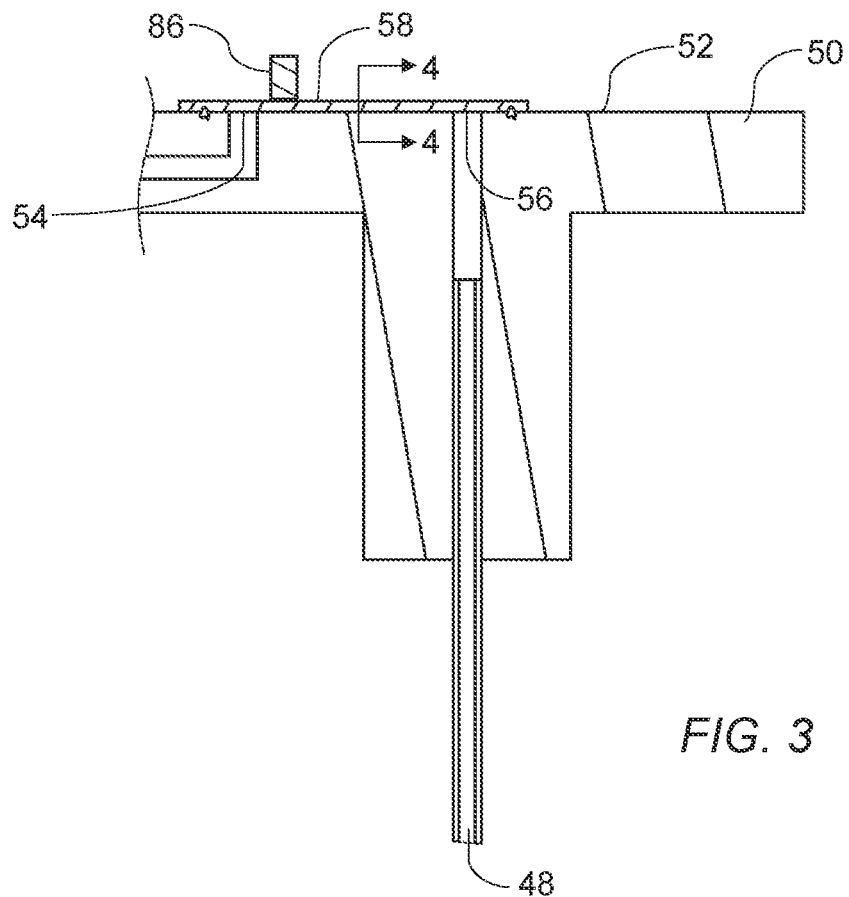
FIG. 3 is an enlarged view in section of the encircled portion 3-3 of the medical pump embodiment of FIG. 1.
Figure 4:
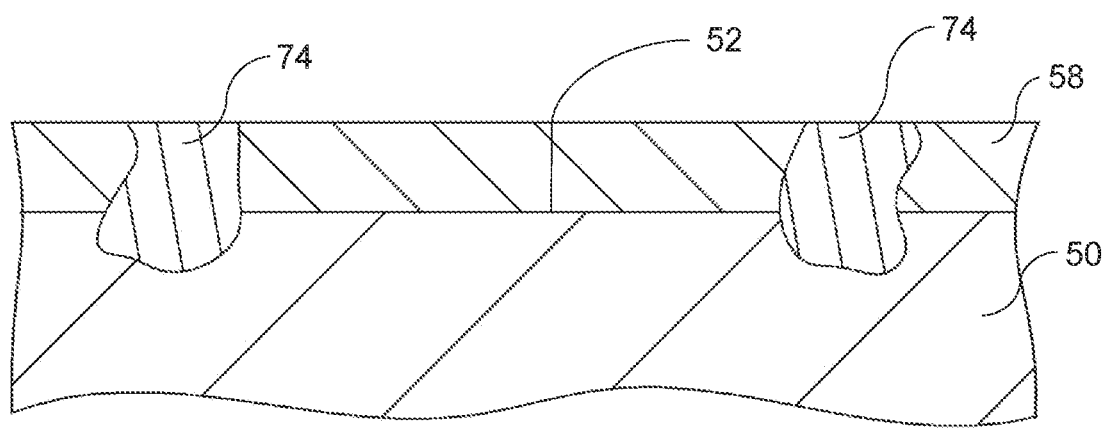
FIG. 4 is an enlarged section view of the flow control valve of FIG. 3 taken along lines 4-4 of FIG. 3.

Other medical pump embodiments may include use of a redundant on/off valve 86 as shown in FIG. 3, pressing against the distensible membrane 58 for example, in line with the distensible membrane 58 of the distensible channel 60 that may be used for flow control. This might allow the distensible channel 60 to be opened or closed as required for flow safety and calibration. It also may create redundancy and verification of the workings of the medical pump system. This redundancy, although adding complexity to the medical pump embodiment 10, may be useful to improve failsafe operation.

Other medical pump embodiments may be configured to displace air with the speaker 20 with a known voltage and displacement characteristics against a flexible liquid pump chamber 18 allowing liquid 12 to flow controllably through the distensible channel 60 of the flow control valve 24 or not, to push liquid 12 to the patient 30 in an open loop type of control system. This system may controllably burp an aliquot of fluid into the patient 30 with a very simple and low cost means of actuation. Redundant controls and feedback may be added if necessary to add features as appropriate. Examples may include, for example, oncology drug delivery, saline delivery and dextrose delivery where accuracy isn't as important as consistent flow over time.

Figure 12:
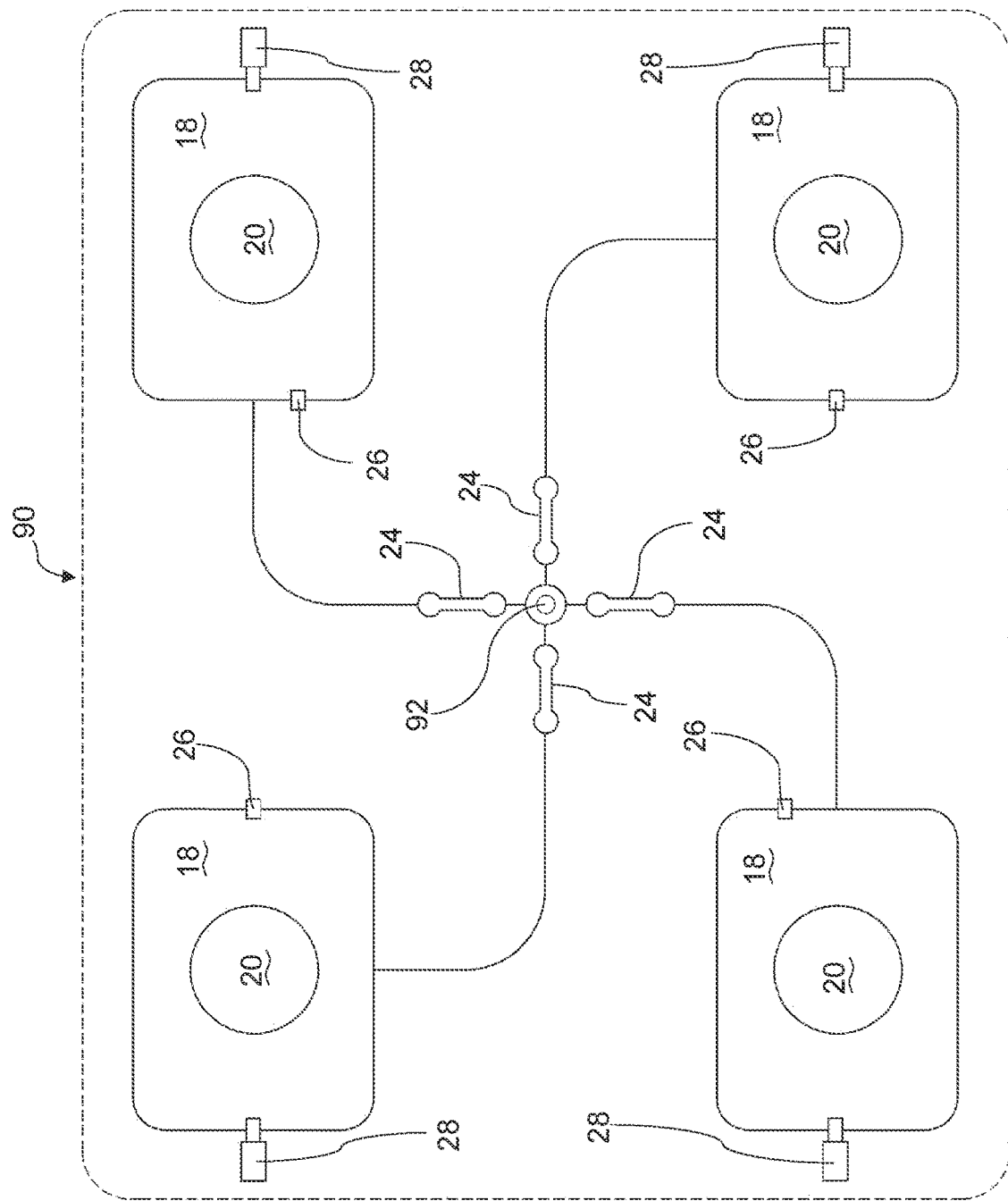
FIG. 12 is a schematic representation of a medical pump having a plurality of pump chambers and respective flow control valves in fluid communication with a common outlet port.

In FIG. 12, a medical pump embodiment 90 having a plurality of pump chambers 18 is shown where the respective liquids 12 of each pump chamber 18 each have a control speaker 20 and a flow control valve 24 and where the liquids 12 pass to a common outlet conduit 92 which may terminate in a common needle or cannula (not shown). The flow control valves 24 may be placed in the center of the medical pump 90 near the common needle for each liquid 12 to pass through, minimizing mixing of the liquids 12 of each of the four liquid pump chambers 18. A flush of saline or other diluent from one of the four chambers could be used to empty or otherwise flush the needle if appropriate.

Some embodiments of a medical pump as shown in FIGS. 13-20 for delivering fluid 12 to a patient 30 may include a pump cavity 102 which is surrounded by a rigid wall 104 and which includes a diaphragm opening 106 at a top portion of the pump cavity 102. A diaphragm 108 may be disposed over and sealed to the diaphragm opening 106 of the pump cavity 102. The medical pump 100 may also include a pump chamber 110 defined by an inside surface of the rigid wall 104 of the pump cavity 102 and an inside surface of the diaphragm 108 which disposed over and sealed to the pump cavity 102. For some embodiments, the diaphragm 108 may include flexible materials such as flexible thermoset polymer, thermoplastic, nylon, silicone, polyvinylchloride (PVC), polypropylene, polyisoprene, polyester or rubber. In some cases, it may be useful for the pump chamber 110 to have an aspect wherein a transverse width of the pump chamber 110 along a direction parallel to the diaphragm 108 is greater than a depth of the pump chamber 110 measured perpendicular to the plane of the diaphragm 108. For some embodiments, the pump chamber 110 may have a width that is about 2 times to about 10 times the depth of the pump chamber 110. In some cases, the pump chamber 110 may include an interior volume of about 50 nanoliters to about 10,000 nanoliters and be configured to pump aliquots of liquid 12 in volumes of about 1 nanoliter to about 1 microliter or more.

A pressure actuator 112, which is generally directed to a device that is configured to impose a force or multiple forces on the diaphragm 108, may include a piston 114 with a distal end that is operatively coupled to the diaphragm 108. In addition, an inlet conduit 116 may also be disposed in fluid communication with the pump chamber 110. A check valve 118 may be operatively coupled to the inlet conduit 116 and may also be oriented to allow a flow of liquid 12 to the pump chamber 110 but prevent a flow of liquid 12 from the pump chamber 110 back towards the check valve 118. Active controllable embodiments of the check valve 118 may be coupled to and operated by a controller such as controller 168 discussed below. Such a check valve 118 may include a passive check valve, an active controllable check valve that may be activated by a signal or energy transmitted to the active check valve or any other suitable form of check valve 118. An outlet conduit 120 may be disposed in fluid communication with the pump chamber 110 and an outlet port 122 disposed in fluid communication with the outlet conduit 120.

The medical pump 100 may further include a flow control valve 124 which is operatively coupled to the outlet conduit 120 between the pump chamber 110 and the outlet port 122. Embodiments of the flow control valve 124 may have the same or similar features, dimensions or materials as those of the flow control valve embodiments 24 discussed above. In particular, embodiments of the flow control valve 124 may serve to act both as a check valve and as a variable flow restrictor with flow characteristics that may be represented generally by the graph shown in FIG. 7 and discussed above. Embodiments of the flow control valve 124 may further include a rigid base 126 having a top surface 128 with an orifice 130 and a distensible membrane 132 secured to the top surface 128 of the rigid base 126 in sealed relation relative to the orifice so as to be in close approximation with the top surface 128 of the rigid base 126. This structure forms a sealed distensible channel 134 between the orifice 130 including the structure surrounding the orifice 130 and an inside surface 136 of the distensible membrane 132, the distensible channel 134 being normally closed. For some embodiments, the outlet conduit 120 may terminate with a tissue interface 138 having an inner lumen 140 in fluid communication with the outlet conduit 120, which in some instances may include a hollow hypodermic needle or cannula 138 configured to be inserted into a patient's tissue 30 such as a patient's dermis, sub-dermis or muscle tissue beneath the patient's skin.

Figure 18:
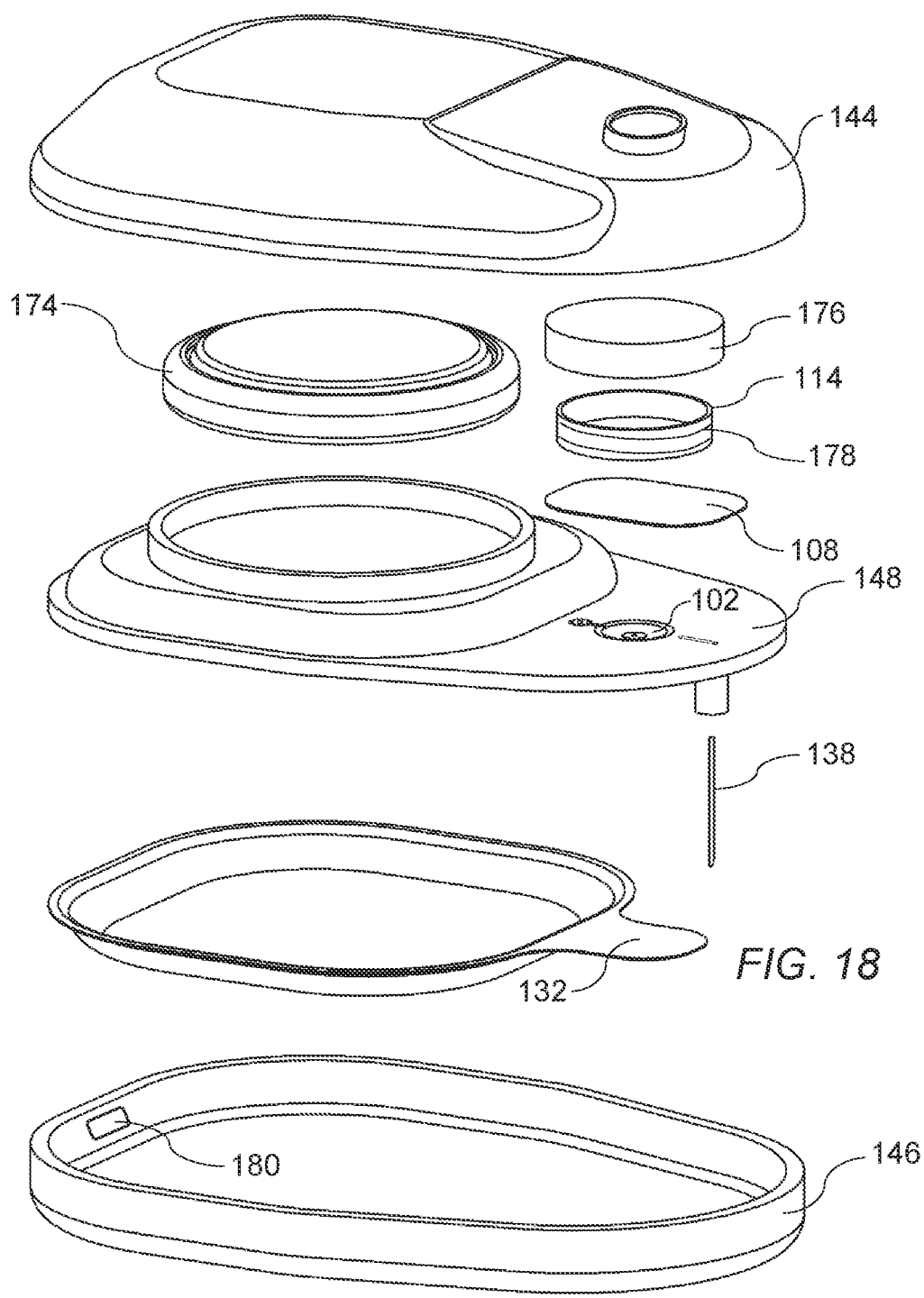
FIG. 18 is an exploded view of the medical pump embodiment of FIG. 13.
Figure 19:
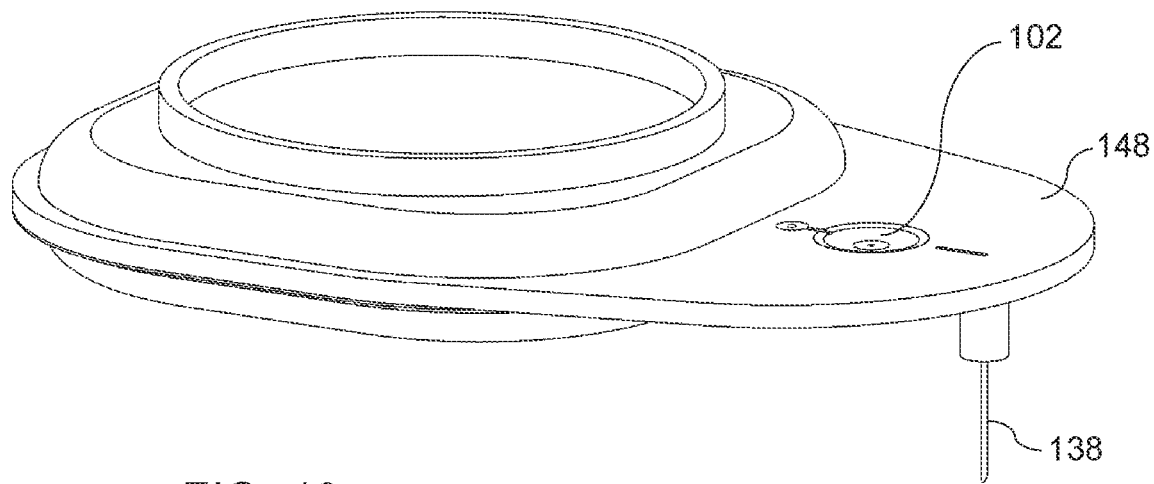
FIG. 19 is a perspective view of a pump chassis of the medical pump embodiment of FIG. 13 showing a pump cavity.
Figure 20:
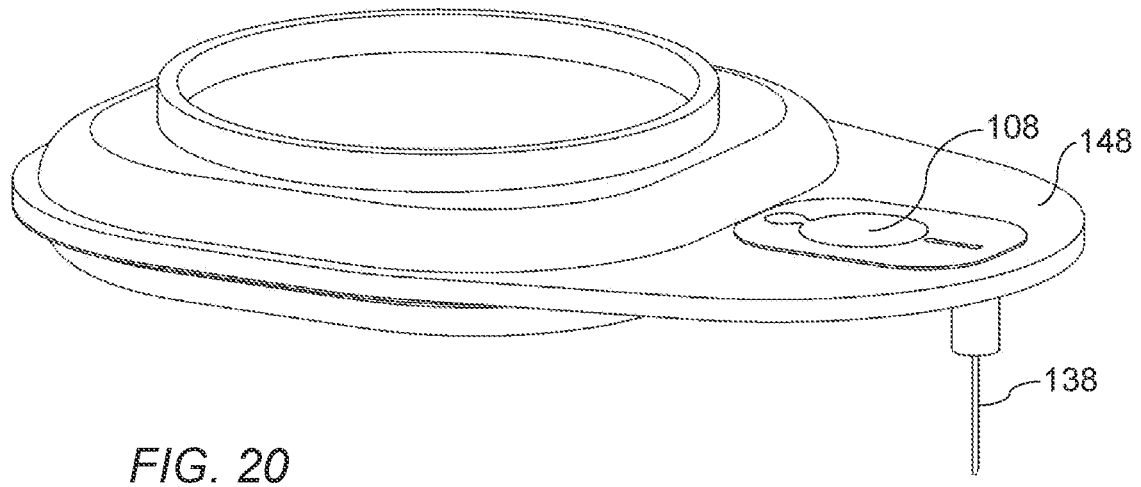
FIG. 20 shows the pump chassis of FIG. 19 with a diaphragm disposed over the pump cavity of the pump chassis.

The components of the medical pump embodiment 100 discussed above may be disposed within or otherwise operatively coupled to a pump housing 142 that includes an upper housing 144, a lower housing 146 and a pump chassis 148 as shown in the exploded view of the medical pump 100 in FIG. 18. The pump housing 142 may be made from any suitable high strength rigid material including polymers such as polycarbonate, acrylonitrile butadiene styrene (ABS) plastic or the like. The pump cavity 102, check valve 118 and flow control valve 124 of the medical pump embodiment 100 may all be formed in whole or at least partially into the structure of the pump chassis 148.

Figure 17:
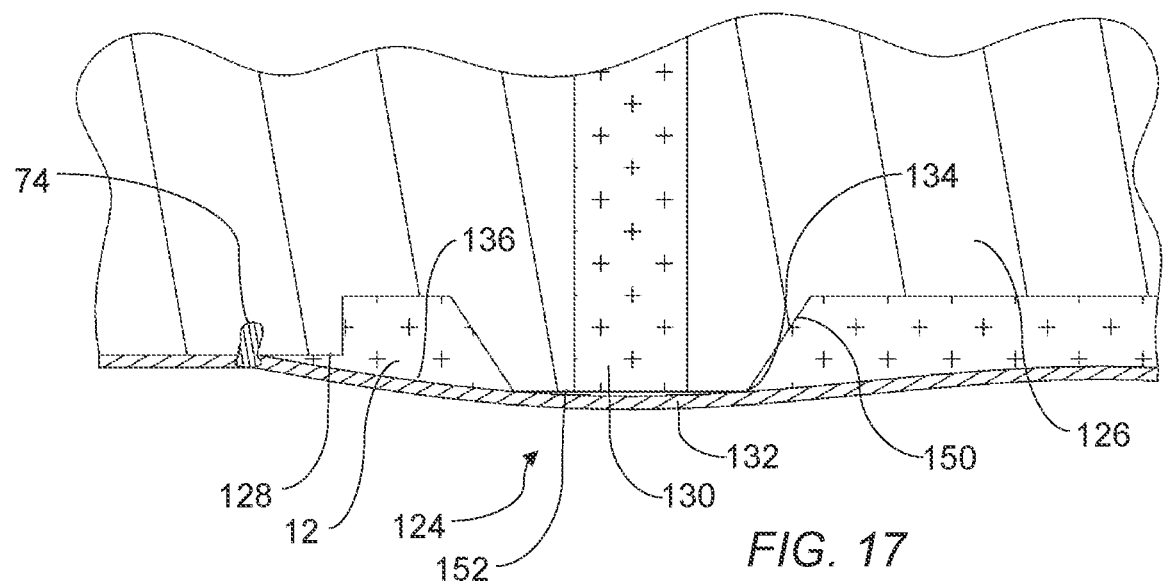
FIG. 17 is an enlarged view in section of a flow control valve embodiment of FIG. 15 and indicated by the encircled portion 17 of FIG. 15, the flow control valve embodiment having a distensible channel formed by a distensible membrane disposed in tension over an orifice of a raised conical boss.

For such embodiments, the flow control valve 124 may further include a raised boss 150 disposed about the orifice 130, the raised boss 150 including a seal surface 152 which is disposed at a level above the top surface 128 of the rigid base 126 and which forms a releasable seal with the distensible membrane 132 as shown in FIG. 17. For some embodiments 100, the distensible channel 134 may include a structure wherein the distensible membrane 132 is secured to the rigid base 126 while the distensible membrane 132 is under some tension in a plane of the distensible membrane 132. In some cases, the distensible membrane 132 may be secured to the rigid base 126 with a weld such as a laser weld 74. The distensible membrane 132 may also be secured to the rigid base 126 by any other suitable means such as ultrasonic welding, solvent welding, heat sealing, adhesive bonding or mechanical capture.

For some embodiments, the distensible membrane 132 of the flow control valve 124 may include a thin polymer or elastomeric material with a thickness of about 0.025 mm to about 1 mm. For some embodiments, the distensible membrane 132 may include materials such as a thermoset polymer, thermoplastic, polyester, polypropylene, PVC, nylon or the like which may be compatible for welding or other forms of bonding to corresponding materials of the rigid base 126 which may include ABS plastic, PC/ABS, cyclic olefin copolymer (COC) or the like.

A reservoir 156 having an interior volume 158 for storing liquids 12 to be delivered to a patient 30 is disposed within the pump housing 142 of the medical pump 100. The interior volume 158 of the reservoir 156 being in fluid communication with the inlet conduit 116. In addition, the check valve 118 is operatively coupled to the inlet conduit 116 between the reservoir 156 and the pump chamber 110 for some embodiments as shown. In some cases, the reservoir 156 may be disposed within an interior volume of a rigid reservoir chamber 160 which may be formed by the pump housing 142 and which may be fluidly sealed from an ambient atmosphere 64.

Figure 14:
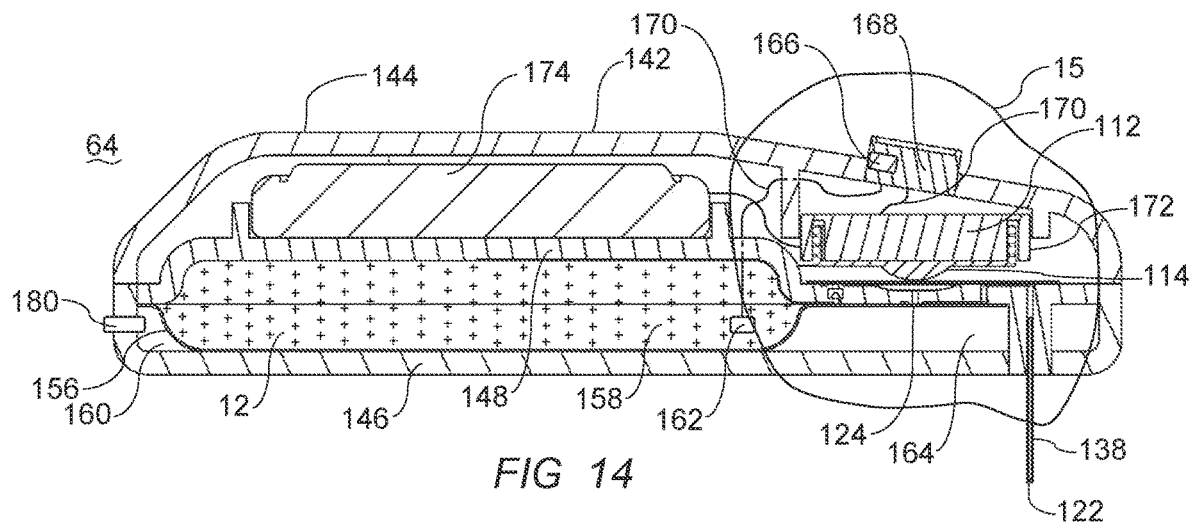
FIG. 14 is a section view of the medical pump embodiment of FIG. 13 taken along lines 14-14 of FIG. 13.
Figure 15:
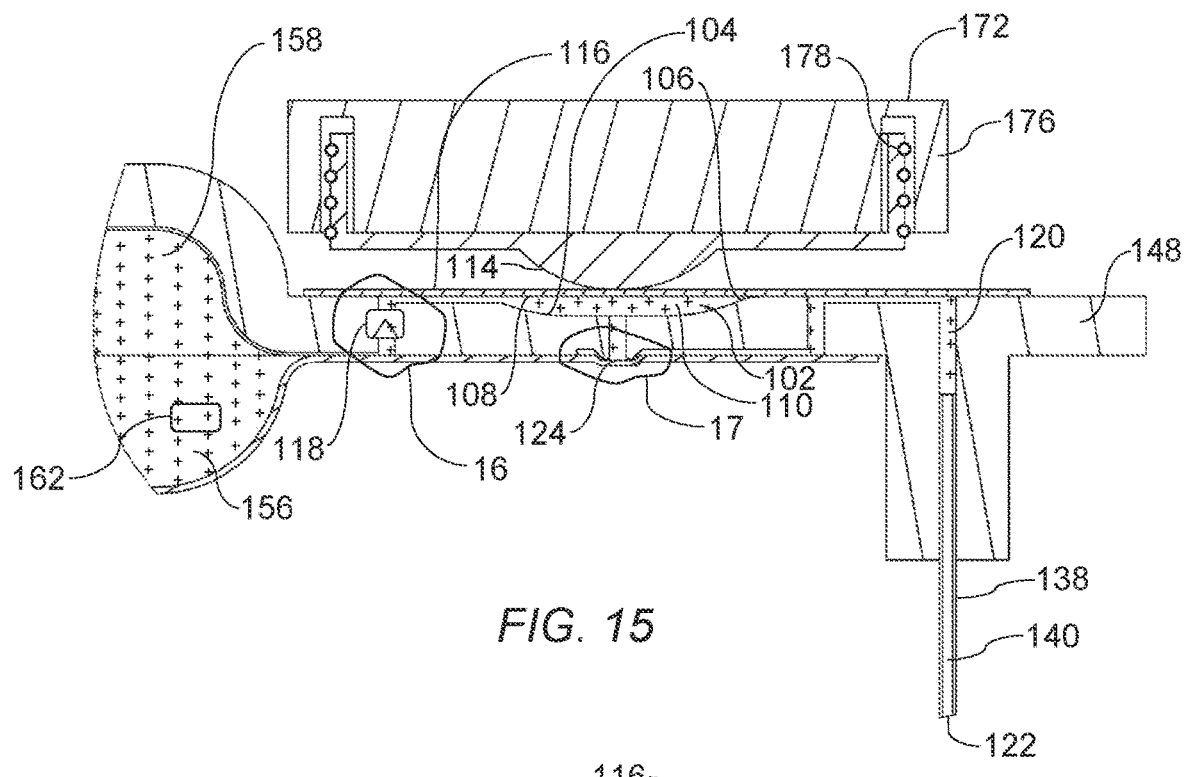
FIG. 15 is an enlarged view in section of a pump section of the medical pump of FIG. 14 indicated by encircled portion 15 of FIG. 14.
Figure 16:
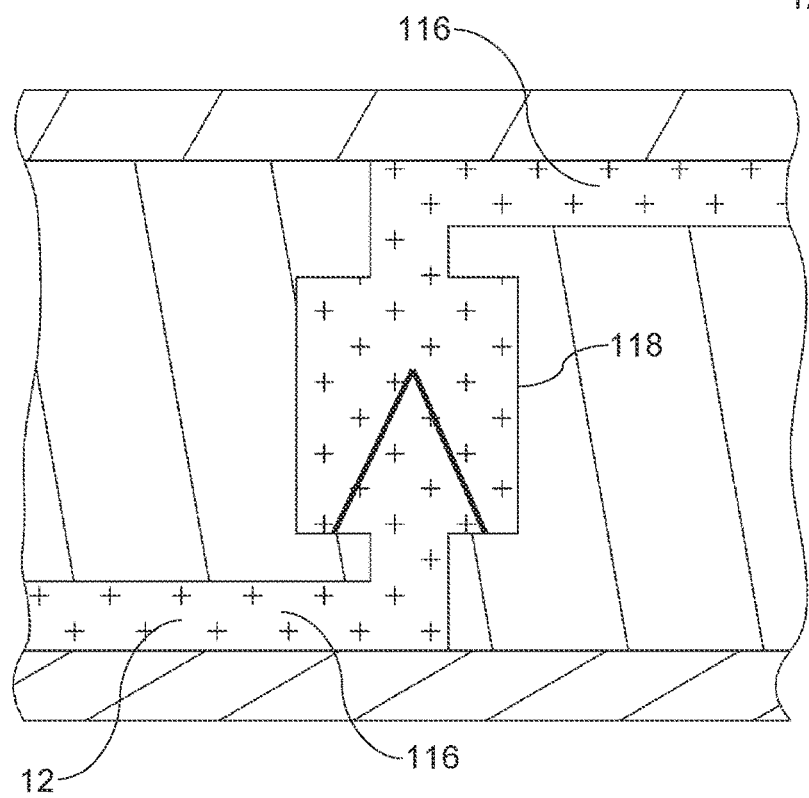
FIG. 16 is an enlarged view in section of a check valve of the medical pump of FIG. 15 indicated by the encircled portion 16 of FIG. 15.

A pressure sensor 162 that is positioned and configured to measure pressure within the interior volume 164 of the rigid reservoir chamber 160 may be disposed within the rigid reservoir chamber 160 and may be coupled to a processor 166 of a controller 168, which may include a micro controller 168, as shown in FIG. 14. For some embodiments, the pressure sensor 162 may be operatively coupled to the controller 168 and configured to measure pressure within the interior volume of the rigid reservoir chamber 160. The controller 168 may further be configured to analyze a pressure profile received from the pressure sensor 162 and calculate an appropriate amount of fluid delivered to a patient based on the pressure profile of pressure change over time and knowledge of the size or volume of the chamber being measured. In some instances, the processor 166 may include software instructions which are configured to process pressure data received from the pressure sensor 162 and determine an amount of fluid 12 delivered to a patient 30 based on pressure change profiles. Such a controller embodiment 168 may also be operatively coupled, such as by electrical wires 170 or the like, to the motor 172 of the pressure actuator 112 and a battery 174 that may be used to store electrical energy for operation of the processor 166, controller 168, motor 172 or any other appropriate element that requires electrical energy for proper operation.

Figure 13:
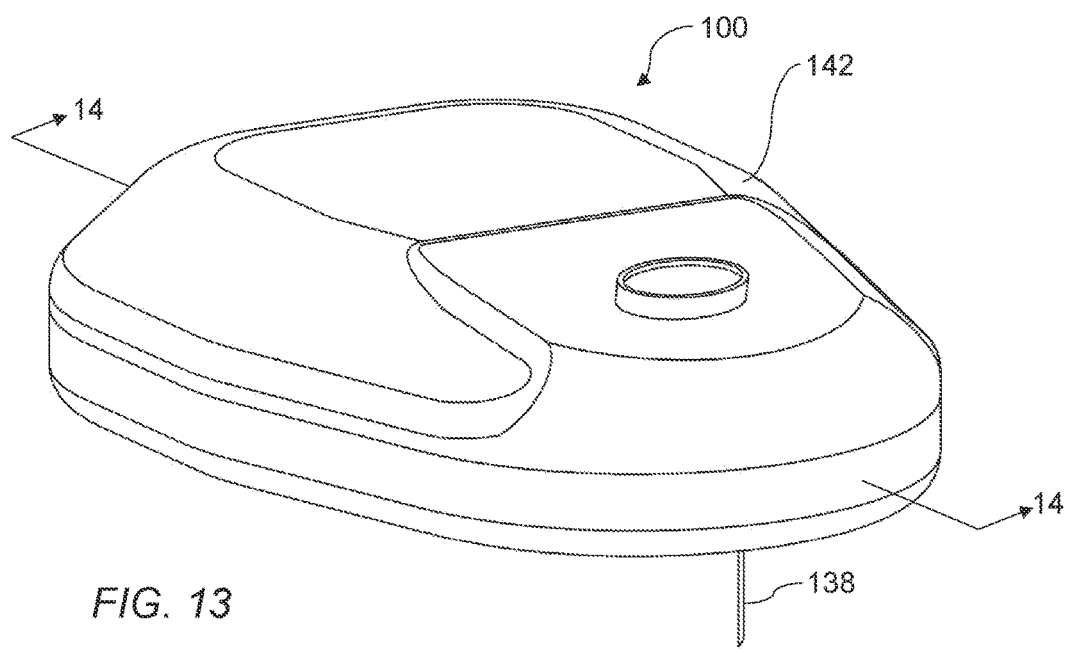
FIG. 13 is a perspective view of a medical pump embodiment.

For certain embodiments, such as the medical pump embodiment 100 illustrated in FIG. 13, the pressure actuator 112 may include a motor 172 which has a magnet 176 and a conducting coil 178 with the conducting coil 178 being operatively coupled to the piston 114 and the magnet 176 secured in a fixed relation to the pump chassis 148 and diaphragm 108. For this configuration, the conducting coil 178 and piston 114 translate towards and away from the diaphragm 108 due to electromagnetic forces between the conducting coil 178 and the magnet 176 when electrical current is conducted through the conducting coil 178. In other embodiments, the magnet 176 may be operatively coupled to the piston 114 instead of the conducting coil 178 and the conducting coil 178 secured in fixed relation to the pump chassis 148 and diaphragm 108.

Another valve 180 may be disposed in operative communication between the interior volume 164 of the rigid reservoir chamber 160 and the ambient atmosphere 64 that surrounds the pump housing 142. Embodiments of such a valve 180 may include an active controllable valve that may be operated or controlled by the controller 168 to open and close at appropriate intervals. For some embodiments, the valve 180 may include a passive small orifice in fluid communication between the interior volume 164 of the rigid reservoir chamber 160 and the ambient atmosphere 64. In some cases, a transverse dimension of such a small orifice opening may be about 0.005 mm to about 0.03 mm. In other embodiments, the valve 180 may include a check valve disposed in fluid communication between the interior volume 164 of the rigid reservoir chamber 160 and the ambient atmosphere 64. Such a check valve 180 being oriented to allow ambient air into the interior volume 164 of the rigid reservoir chamber 160.

As discussed above, the interior volume 158 of the reservoir 156 may be used to store any suitable liquid 12 for delivery to the body of a patient 30, including non-bioactive liquids such as saline, dextrose and the like, or bioactive liquids including medicaments such as insulin, antibiotics, peptides, pain medication, and the like. For some embodiments, the interior volume 158 of the reservoir 156 may be about 0.25 milliliters to about 20 milliliters, more specifically, about 1 milliliter to about 15 milliliters.

Figure 27:
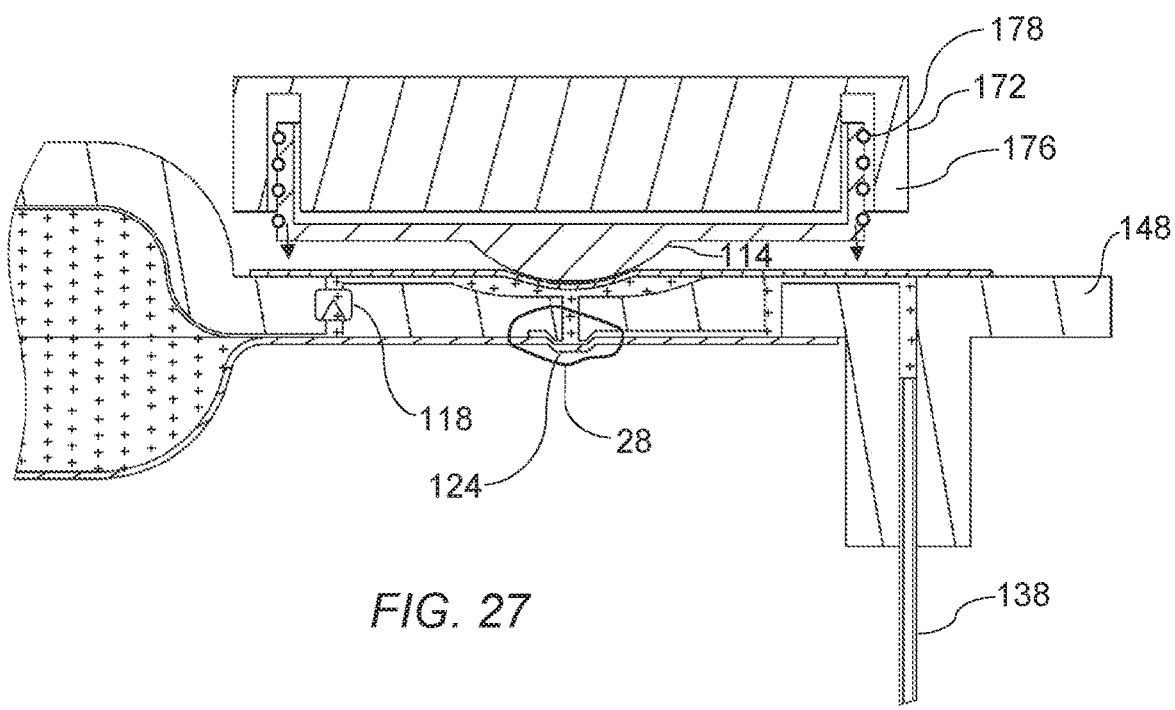
FIG. 27 is an enlarged view in section of a pump cavity portion of the medical pump of FIG. 26 taken along lines 27-27 of FIG. 26.

Some embodiments of a method of pumping a liquid 12 from a medical pump 100 to the patient as shown in FIGS. 25-31 may include actuating the motor 172 of the pressure actuator 112 and advancing the piston 114 of the pressure actuator 112 into the diaphragm 108 of a pump chamber 110. The piston 114 may continue to be advanced until an inside surface of the diaphragm 108 intrudes into an interior volume of the pump chamber 110 thereby reducing the interior volume of the pump chamber 110, increasing an internal pressure within an interior volume of the pump chamber 110 and expelling the liquid 12 from the pump chamber 110 and into the outlet conduit 120 as shown in FIG. 27. The method may also include flowing the liquid expelled from the pump chamber 110 through the outlet conduit 120 and into the distensible channel 134 of the flow control valve 124 which is normally closed. For some embodiments, the flow control valve 124 that is normally closed is closed sufficiently in order to prevent a clinically significant amount of liquid 12 from being dispensed from the medical pump 100. For some embodiments, the distensible channel 134 may function as a check valve wherein flow from the pump chamber 110 through the flow control valve 124 does not begin until a cracking pressure of the distensible channel 134 is reached and overcome and the distensible channel 134 opens from the normally closed state.

Figure 28:
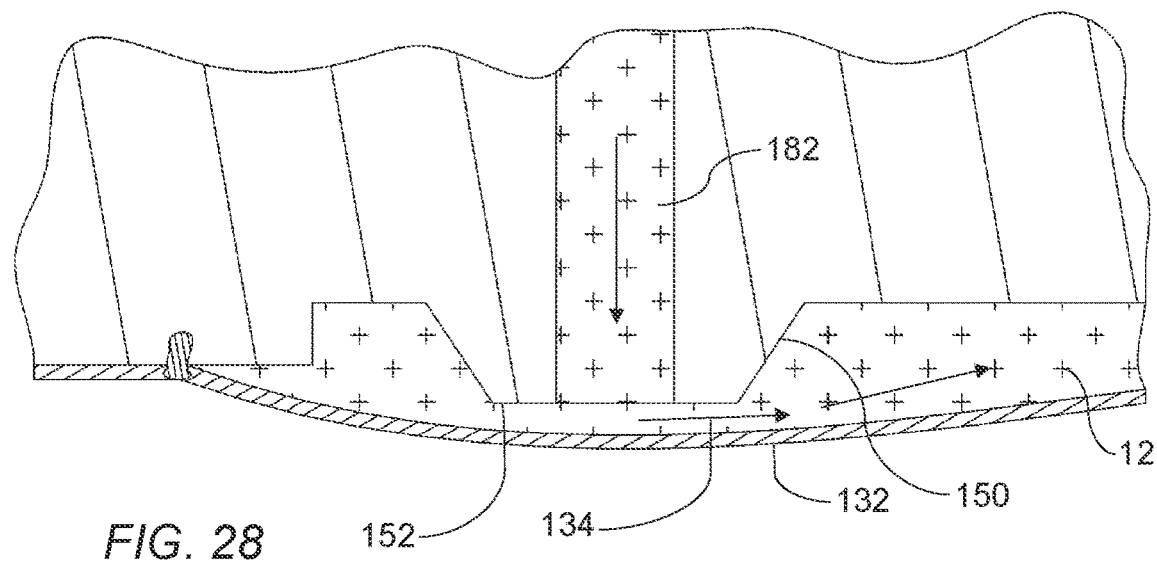
FIG. 28 is an enlarged view in section of the distensible channel of FIG. 27 in an open state taken along lines 28-28 of FIG. 27.

The flowing of the liquid 12 into the distensible channel 134, as indicated by the arrows shown in FIG. 28, results in stretching the distensible membrane 132 of the flow control valve 124 and expanding the distensible channel 134 to allow a flow of the liquid 12 through the flow control valve 124 and out of an outlet port 122 of the outlet conduit 120. Such stretching or compliance of the distensible membrane 132 may result in a non-linear flow response as a function of pressure change such as is exemplified in the flow graph of FIG. 7. For some embodiments, the distensible channel 134 may include a distensible membrane 132 under tension disposed over the orifice 130 of the raised boss 150 of the flow control valve 124 with the distensible membrane 132 sealing the orifice 130. For such embodiments, expanding the distensible channel 134 to allow a flow of the liquid 12 through the flow control valve 124 may include pressurizing liquid 12 within a lumen 182 of the raised boss 150 and pushing the distensible membrane 132 away from the orifice 130 thereby opening the orifice 130 as shown in FIG. 28. For such a method, the amount of liquid 12 that is pumped may be controlled by selecting the amount of pressure applied by the piston 114 to the diaphragm 108 and the amount of time the pressure is applied by the piston 114. For electromagnetic conducting coil embodiments of the motor 172, these parameters may be controlled by adjusting the voltage and dwell of the electrical current conducted through the coil 178.

Figure 29:
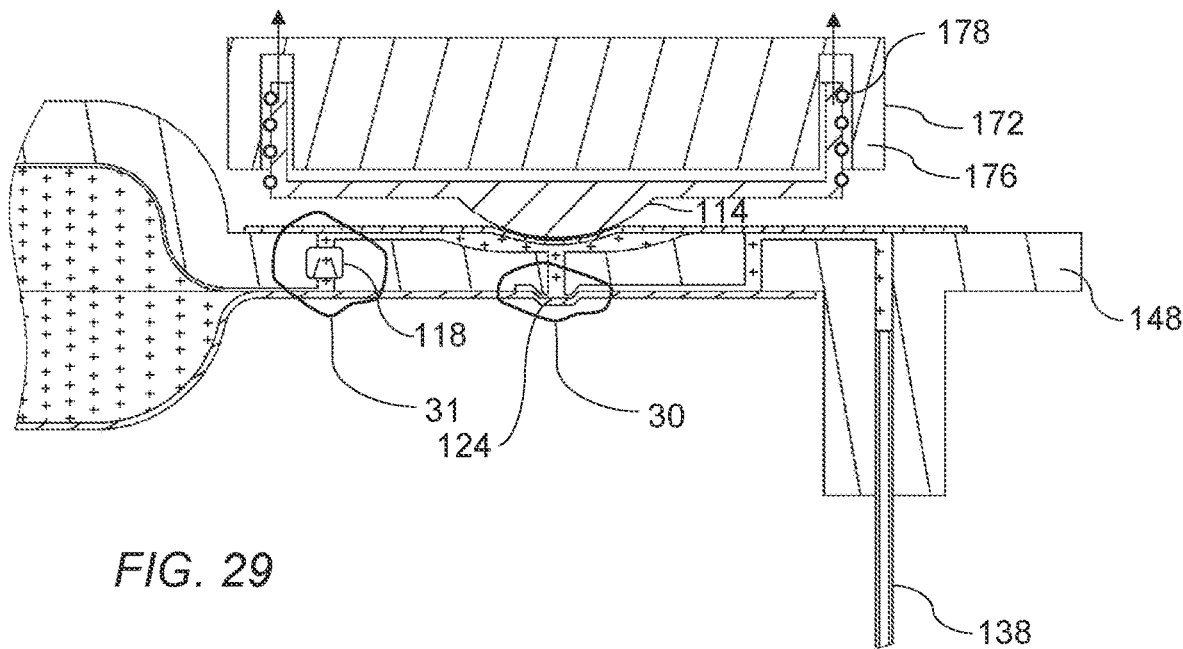
FIG. 29 is an enlarged view in section of the pump cavity portion of FIG. 27 with a check valve embodiment of the medical pump in an open state and a distensible channel of the flow control valve in a closed state.
Figure 30:
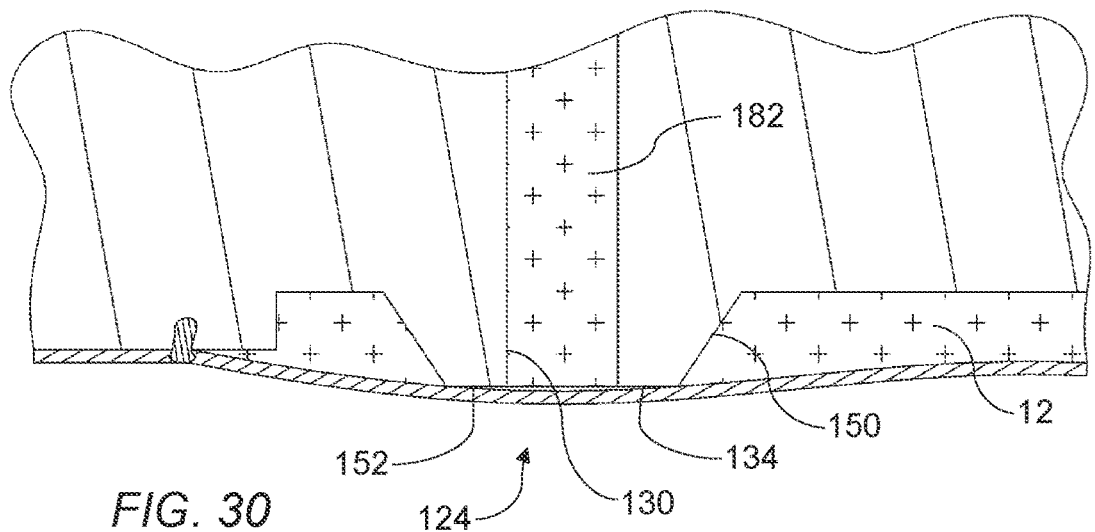
FIG. 30 is an enlarged view of the flow control valve of FIG. 29 indicated by the encircled portion 30 off FIG. 29.
Figure 31:
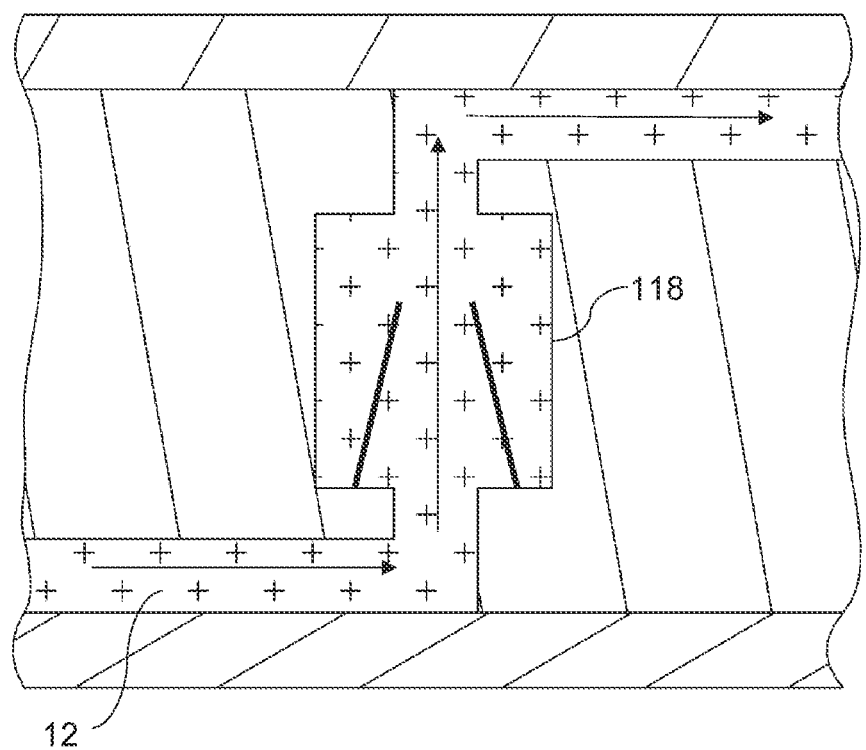
FIG. 31 is an enlarged view of the check valve of FIG. 29 indicated by the encircled portion 31 off FIG. 29.

Such a method of pumping a liquid 12 from the medical pump 100 may further include withdrawing the piston 114 of the pressure actuator 112 away from the diaphragm 108 as shown in FIG. 29 by reversing or reducing the current applied to the coil 178 of the motor 172 and thereby contracting the diaphragm 108 from a stretched state and increasing the interior volume of the pump chamber 110. Withdrawing the piston 114 in this manner has the effect of reducing liquid pressure on the distensible membrane 132 of the flow control valve 124. This reduced fluid pressure may then allow the distensible channel 134 to assume the normally closed state while also drawing liquid through the inlet conduit 116 and a check valve 118 disposed in fluid communication with the inlet conduit 116 into the pump chamber 110 thereby refilling the pump chamber 110 as shown in FIG. 30 and as indicated by the flow arrows in FIG. 31.

In some cases, drawing liquid 12 through the inlet conduit 116 may also include drawing liquid 12 from within the interior volume 158 of the reservoir 156 which is disposed within the sealed rigid reservoir chamber 160 of the medical pump housing 142. For such a process, pressure may be measured within the interior volume 164 of the rigid reservoir chamber 160 before and after drawing the liquid 12 through the inlet conduit 116. Information regarding a measured pressure drop over time may be used by the processor 166 of the controller 168 to determine an amount of liquid 12 dispensed. In addition, in some cases, the electrical current conducted through the conducting coil 178 may be controlled by the controller 168 permitting precise displacement of the piston 114 and precise control of a force exerted by the piston 114 on the diaphragm 108. For such embodiments, a measured potential voltage may be used to determine a resistance value of electrical current through the conducting coil 178 and thereafter determining whether inefficiencies in performance are present which may be indicative of an occlusion of the outlet conduit 120.

Figure 21:
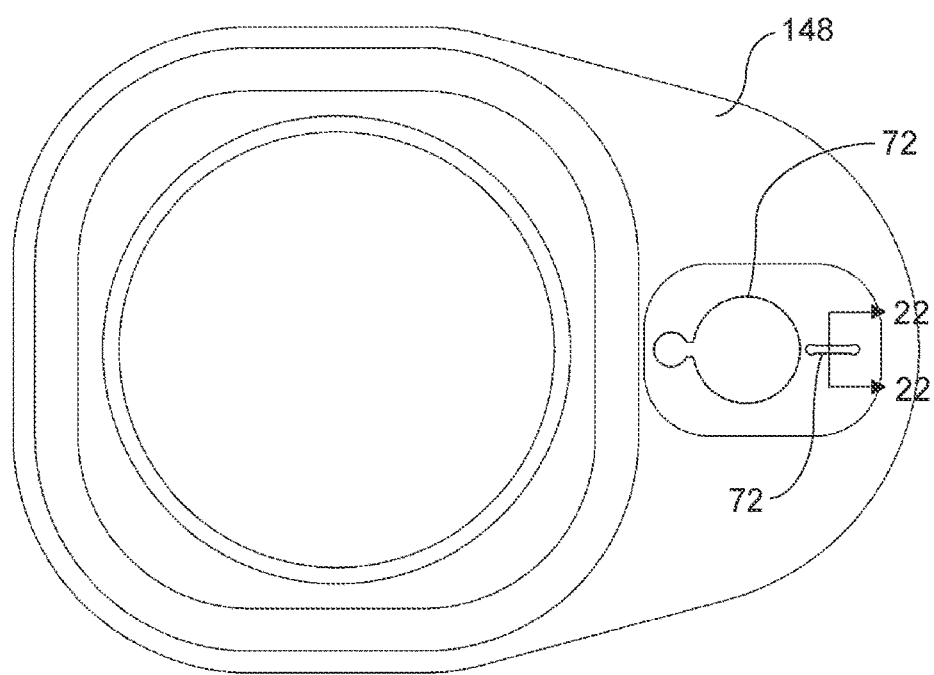
FIG. 21 is a top view of the pump chassis of FIG. 19 showing the diaphragm disposed in tension over the pump cavity and a weld pattern for the formation of the pump chamber.
Figure 22:
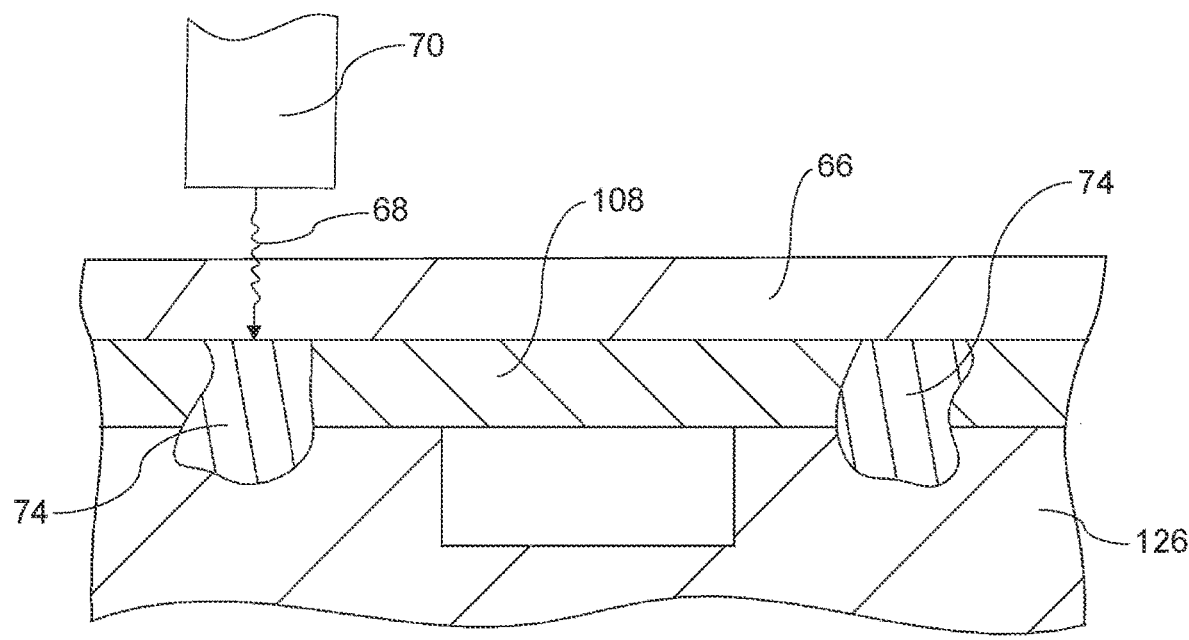
FIG. 22 is a section view indicated by lines 22-22 of FIG. 21 of a laser welding process, as an example, applied to diaphragm material and rigid base material through a layer of rigid material.
Figure 23:
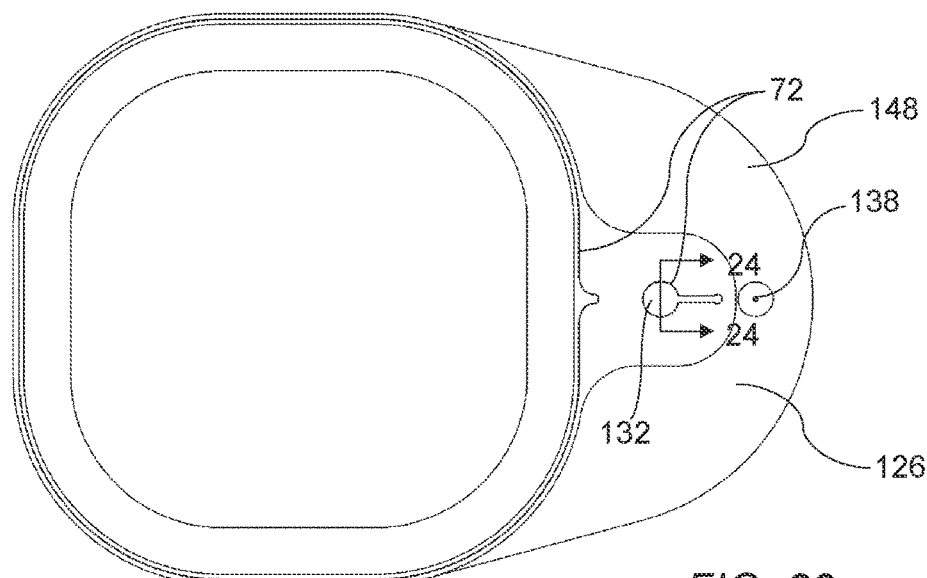
FIG. 23 is a bottom view of the pump chassis of FIG. 19 with a distensible membrane disposed over an orifice of a raised conical boss to form a distensible channel of a flow control valve in fluid communication with an outlet conduit of the pump chamber.
Figure 24:
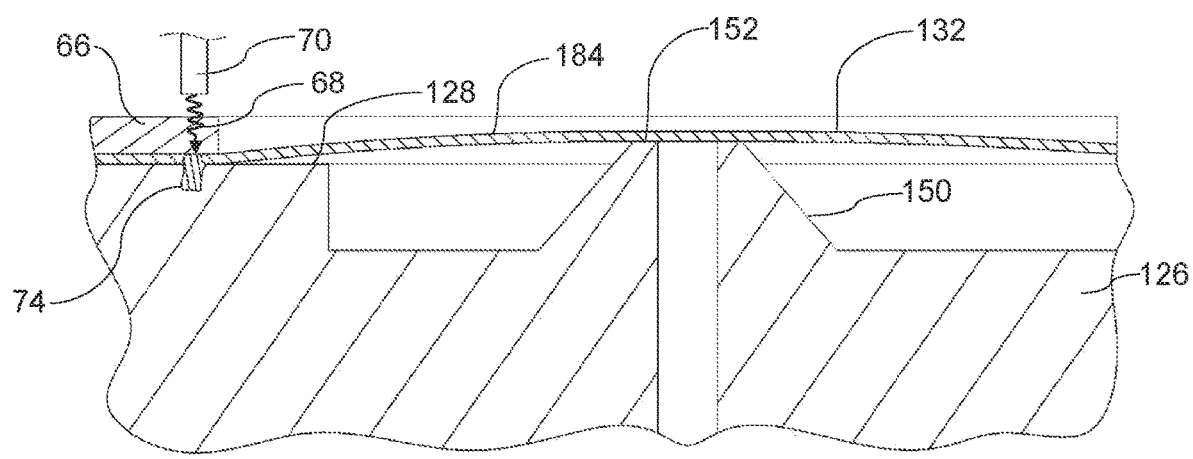
FIG. 24 is a section view indicated by lines 24-24 of FIG. 23 illustrating laser energy being transmitted to a weld zone between the distensible membrane and rigid base of the flow control valve through a layer of rigid material.

Some embodiments of a method of welding a distensible membrane 132 to the rigid base 126 of the pump cavity 110 as shown generally in FIGS. 8-10 and 21-24 may include positioning the distensible membrane 132 onto a top surface 128 of the rigid base 126 such that an inside surface of the distensible membrane 132 is in contact with the top surface 128 of the rigid base 126 as shown in FIGS. 23 and 24. Thereafter, a layer of rigid material 66 may be positioned onto an outside surface 184 of the distensible membrane 132 over an area between the distensible membrane 132 and rigid base 126 to be welded. The layer of rigid material 66 may optionally include rigid transparent material 66. The method may further include applying pressure to the distensible membrane 132 in a direction towards the rigid base 126 thereby approximating the inside surface of the distensible membrane 132 with the top surface 128 of the rigid base 126 and transmitting electromagnetic energy 68 through the layer of rigid material 66 and onto the distensible membrane 132 until the distensible membrane 132 and rigid base 126 melt and form a fluid tight weld zone 74. In some cases, the layer of material 66 may be positioned so as to provide a predetermined minimum pressure on the distensible membrane 132 prior to welding.

In some cases, positioning the layer of rigid material 66 onto the outside surface 184 of the distensible membrane 132 may include positioning a glass plate 66 onto the outside surface 184 of the distensible membrane 132 over an area between the distensible membrane 132 and rigid base 126 to be welded. In addition, in some instances, transmitting electromagnetic energy 68 through the layer of rigid material 66 and onto the distensible membrane 132 includes transmitting laser energy 68 through the layer of rigid material 66 and onto and at least partially through the distensible membrane 132. For some flow control valve embodiments 124, positioning the distensible membrane 132 onto a top surface 128 of the rigid base 126 includes positioning a distensible membrane 132 that includes thin polymer film over a pump cavity 102 of a rigid base 126 made of a polymer. In some cases, positioning the distensible membrane 132 onto a top surface 128 of the rigid base 126 includes positioning the distensible membrane 132 over a flat planar surface 128 of the rigid base 126 and welding a perimeter configuration of weld lines 72 so as to form a sealed distensible channel 134 between the inside surface of the distensible membrane 132 and top surface 128 of the rigid base 126 within the weld perimeter. For the medical pump embodiment 100, the process of welding the diaphragm 108 over the pump cavity 102 disposed in the pump chassis 148 in order to form the pump chamber 110 as shown in FIGS. 21 and 22 may be the same as or similar to the method discussed above with regard to the welding of the distensible membrane 132 to the rigid base 126 including laser welding. Such methods may also include heat sealing, ultrasonic welding, solvent welding, adhesive bonding, mechanical capture or the like.

For some embodiments, heat may be applied to the distensible membrane 132 after the distensible membrane 132 has been welded to the rigid base 126 in order to increase tension one the distensible membrane 132 and increase an equivalent spring rate of the distensible membrane 132. Such a post processing heat treatment may be used to adjust fluid flow characteristics of a distensible channel produced by the method. In addition, in some cases, negative air pressure may be applied between the distensible membrane 132 and the rigid base 126 to tightly form the distensible membrane 132 onto the rigid base 126 providing a preset position on the material of the distensible membrane 132 of the features of the rigid base 126. In some instances, the distensible membrane 132 may be preformed prior to positioning the distensible membrane 132 onto the top surface of the rigid base 126.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions, which have been employed, are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. A medical pump for delivering fluid to a patient, comprising:
    a pump cavity which is surrounded by a rigid wall and which includes a diaphragm opening;
    a diaphragm disposed over and sealed to the diaphragm opening of the pump cavity;
    a pump chamber defined by an inside surface of the rigid wall of the pump cavity and an inside surface of the diaphragm which disposed over and sealed to the pump cavity;
    a pressure actuator including a piston with a distal end that is operatively coupled to the diaphragm;
    an inlet conduit which is in fluid communication with the pump chamber;
    a check valve which is operatively coupled to the inlet conduit and which is oriented to allow a flow of liquid to the pump chamber but prevent a flow of liquid from the pump chamber back towards the check valve;
    an outlet conduit which is in fluid communication with the pump chamber;
    an outlet port which is in fluid communication with the outlet conduit; and
    a flow control valve which is operatively coupled to the outlet conduit between the pump chamber and the outlet port, the flow control valve comprising:
        a rigid base having a surface and an orifice disposed adjacent the surface, and
        a distensible membrane secured to the surface of the rigid base in a normally closed relation relative to the orifice so as to be in approximation with the surface of the rigid base forming a sealed distensible channel between the orifice and an inside surface of the distensible membrane, the distensible membrane being normally closed.

2. The medical pump of claim 1 wherein the flow control valve further comprises a raised boss disposed about the orifice, the raised boss including a seal surface which is disposed above the surface of the rigid base and which forms a releasable seal with the distensible membrane.

3. The medical pump of claim 1 further comprising a reservoir including an interior volume which is in fluid communication with the inlet conduit and wherein the check valve is operatively coupled to the inlet conduit between the reservoir and the pump chamber.

4. The medical pump of claim 3 wherein the reservoir is disposed within an interior volume of a rigid reservoir chamber which is fluidly sealed from an ambient atmosphere and which further includes a pressure sensor that measures pressure within the interior volume of the rigid reservoir chamber and that is coupled to a controller.

5. The medical pump of claim 4 wherein the controller is configured to analyze a pressure profile received from the pressure sensor and calculate an appropriate amount of fluid delivered to a patient.

6. The medical pump of claim 4 further comprising a valve disposed in operative communication between the interior volume of the rigid reservoir chamber and the ambient atmosphere.

7. The medical pump of claim 6 wherein the valve disposed in operative communication between the interior volume of the rigid reservoir chamber and the ambient atmosphere comprises an active controllable valve disposed in fluid communication between the interior volume of the rigid reservoir chamber and the ambient atmosphere.

8. The medical pump of claim 6 wherein the valve disposed in operative communication between the interior volume of the rigid reservoir chamber and the ambient atmosphere comprises a passive orifice in fluid communication between the interior volume of the rigid reservoir chamber and the ambient atmosphere.

9. The medical pump of claim 6 wherein the valve disposed in operative communication between the interior volume of the rigid reservoir chamber and the ambient atmosphere comprises a check valve disposed in fluid communication between the interior volume of the rigid reservoir chamber and the ambient atmosphere and oriented to allow ambient air into the interior volume of the rigid reservoir chamber.

10. The medical pump of claim 1 further comprising a tissue interface having a lumen in fluid the outlet conduit.

11. The medical pump of claim 1 wherein the distensible channel comprises the distensible membrane secured to the rigid base under tension.

* * * * *